US012733864B2

(12) United States Patent
Zaldua et al.

(10) Patent No.: US 12,733,864 B2
(45) Date of Patent: Sep. 15, 2026

(54) DETECTION OF COGNITIVE IMPAIRMENT

(71) Applicant: ACCEXIBLE IMPACTO S.L., Urduliz (ES)

(72) Inventors: Javier Zaldua, Bilbao (ES); Carla Zaldua, Bilbao (ES); Javier Jiménez, Bilbao (ES); Pablo De La Guardia, Bilbao (ES); Alberto J. Coca, Bilbao (ES); Victor Adan, Bilbao (ES); Carmen García Mateo, Bilbao (ES); Laura Docio, Bilbao (ES); Pedro Montejo, Bilbao (ES)

(73) Assignee: ACCEXIBLE IMPACTO S.L., Urduliz (ES)

( * ) Notice: Subject to any disclaimer, the term of this patent is extended or adjusted under 35 U.S.C. 154(b) by 0 days.

(21) Appl. No.: 18/039,913

(22) PCT Filed: Nov. 26, 2021

(86) PCT No.: PCT/EP2021/083125
§ 371 (c)(1),
(2) Date: Jun. 1, 2023

(87) PCT Pub. No.: WO2022/117444
PCT Pub. Date: Jun. 9, 2022

(65) Prior Publication Data

US 2024/0023877 A1 Jan. 25, 2024

(30) Foreign Application Priority Data

Dec. 2, 2020 (GB) ..................................... 2019000

(51) Int. Cl.
*A61B 5/00* (2006.01)
*G10L 15/06* (2013.01)
(Continued)

(52) U.S. Cl.
CPC .......... *A61B 5/4088* (2013.01); *A61B 5/4803* (2013.01); *A61B 5/7267* (2013.01);
(Continued)

(58) Field of Classification Search
CPC ................ A61B 5/4088; A61B 5/4803; A61B 5/7267; A61B 5/7475; A61B 5/0002;
(Continued)

(56) References Cited

U.S. PATENT DOCUMENTS 7,925,508 B1 * 4/2011 Michaelis ............... G10L 17/26 600/300
9,883,831 B1 * 2/2018 Stewart ................ A61B 5/4088
(Continued)

FOREIGN PATENT DOCUMENTS

EP 3 809 411 A1 4/2021
JP 2019-084249 6/2019
WO WO-2013/138633 9/2013

OTHER PUBLICATIONS

Dos Santos et al., "Enriching Complex Networks with Word Embeddings for Detecting Mild Cognitive Impairment from Speech Transcripts," (2017), arXiv.ORG, Cornell University Library, 201 Olin Library Cornell University Ithaca, NY 14853, 13 pages.
(Continued)

*Primary Examiner* — Jack Yip
(74) *Attorney, Agent, or Firm* — Foley & Lardner LLP

(57) ABSTRACT

A computer-implemented method (1) of detecting cognitive impairment comprising: receiving audio data (21) representing recorded utterances of a patient; processing the audio data using a speech-to-text engine (30) to produce a text transcription (301) of the recorded utterances; processing the text transcription to calculate (41) a plurality of test variables (411) associated with a neuropsychological test; calculating, by applying a trained detection model (51) on the
(Continued)

plurality of test variables, an impairment probability (511) indicating a likelihood that the patient suffers from the cognitive impairment; and indicating that the patient suffers from the cognitive impairment if a final impairment probability based on the impairment probability is above a predetermined threshold, and indicating that the patient does not suffer from the cognitive impairment if the final impairment probability is below the predetermined threshold.

20 Claims, 8 Drawing Sheets

(51) Int. Cl.
*G10L 15/18* (2013.01)
*G10L 25/66* (2013.01)
*G16H 20/70* (2018.01)
*G16H 50/20* (2018.01)

(52) U.S. Cl.
CPC .......... *A61B 5/7475* (2013.01); *G10L 15/063* (2013.01); *G10L 15/1815* (2013.01); *G10L 25/66* (2013.01); *G16H 20/70* (2018.01); *G16H 50/20* (2018.01); *A61B 5/0002* (2013.01)

(58) Field of Classification Search
CPC ................ A61B 5/7264; G10L 15/063; G10L 15/1815; G10L 25/66; G10L 15/26; G16H 20/70; G16H 50/20; G16H 10/20
See application file for complete search history.

(56) References Cited

U.S. PATENT DOCUMENTS

| | | | | |
|---|---|---|---|---|
| 2005/0187436 | A1* | 8/2005 | Doniger | A61B 5/16 128/920 |
| 2010/0292545 | A1* | 11/2010 | Berka | A61B 5/374 600/301 |
| 2011/0081640 | A1* | 4/2011 | Tseng | G06Q 30/04 434/362 |
| 2015/0112232 | A1* | 4/2015 | Quatieri | A61B 5/7264 600/595 |
| 2018/0322894 | A1* | 11/2018 | Kim | G16H 80/00 |
| 2018/0322961 | A1 | 11/2018 | Kim et al. | |
| 2018/0322964 | A1 | 11/2018 | Leblanc | |
| 2019/0311815 | A1* | 10/2019 | Kim | G16H 10/20 |
| 2019/0385711 | A1* | 12/2019 | Shriberg | G16H 15/00 |
| 2020/0118458 | A1* | 4/2020 | Shriberg | G16H 40/67 |
| 2020/0345290 | A1 | 11/2020 | Vignisson et al. | |
| 2021/0133509 | A1* | 5/2021 | Wall | G16H 50/20 |
| 2021/0369163 | A1* | 12/2021 | Hu | A61B 5/7264 |
| 2022/0076694 | A1* | 3/2022 | Pijl | G16H 40/67 |
| 2023/0045078 | A1* | 2/2023 | Berisha | A61B 5/486 |

OTHER PUBLICATIONS

Fraser et al., "Linguistic Features Identify Alzheimer's Disease in Narrative Speech," (2016), Journal of Alzheimer's Disease 49, pp. 407-422.
International Search Report dated Jul. 3, 2022 from appl. No. PCT/EP2021/083125.
Leandro B Dos Santos et al: "Enriching Complex Networks with Word Embeddings for Detecting Mild Cognitive Impairment from Speech Transcripts", arxiv.org, Cornell University, Apr. 26, 2017, p. 2, 5, 7 & 9.
Lopez-Otero et al., "Assessing speaker independence on a speech-based depression level estimation system," (2015), Pattern Recognition Letters 68, pp. 343-350.
Lopez-Otero et al., "Influence of speaker de-identification in depression detection," (2017), IET Signal Processing, vol. 11, Issue 9, pp. 1023-1030.
Morris et al., "The Consortium to Establish a Registry for Alzheimer's Disease (CERAD). Part I. Clinical and neuropsychological assessment of Alzheimer's disease," (1989) Neurology 39, pp. 1159%u20131165.
Ortega-Garcia et al., "The Multiscenario Multienvironment BioSecure Multimodal Database (BMDB)," (2010), IEEE Transactions on Pattern Analysis and Machine Intelligence, vol. 32, No. 6, pp. 1097-1111.
Troger et al., "Exploitation vs. exploration-computational temporal and semantic analysis explains semantic verbal fluency impairment in Alzheimer's disease," (2019), Neuropsychologia 131, pp. 53-61.
Troyer et al., "Clustering and Switching as Two Components of Verbal Fluency: Evidence From Younger and Older Healthy Adults," (1997), Neuropsychology vol. 11, No. 1, pp. 138-146.
Valstar et al., "AVEC 2013: The Continuous Audio/Visual Emotion and Depression Recognition Challenge," (2013), ACM 978-1-4503-2395—Jun. 13, 2010, http://dx.doi.org/10.1145/2512530.2512533, pp. 3-10.
Various authors, "Montreal Cognitive Assessment," (2020), Wikipedia, available at https://en.wikipedia.org/w/index.php?title=Montreal_Cognitive_Assessment&oldid=976763474 [Accessed May 27, 2021].
Various authors, "Verbal fluency test," (2020), Wikipedia, available at https://en.wikipedia.org/w/index.php?title=Verbal_fluency_test&oldid=985493768 [Accessed May 27, 2021].
Vaughan et al., "Preservation of the Semantic Verbal Fluency Advantage in a Large Population-Based Sample: Normative Data from the TILDA Study," (2016), Journal of the International Neuropsychological Society, pp. 570-576.

* cited by examiner

DETECTION OF COGNITIVE IMPAIRMENT

CROSS-REFERENCE TO RELATED APPLICATIONS

This application is a U.S. National Stage Application under 35 U.S.C. § 371 of International Patent Application No. PCT/EP2021/083125, filed Nov. 26, 2021, which claims the benefit of and priority to Great Britain Patent Application No. GB2019000.5, filed Dec. 2, 2020, the entire disclosure of each of which is incorporated by reference herein.

FIELD

The present invention relates to detection of cognitive impairment, including mild cognitive impairment and dementia. There is disclosed a computer-implemented method of detecting cognitive impairment, a method of training a detection model for use in a neuropsychological test for detecting cognitive impairment, and a system for executing the method of detecting cognitive impairment.

BACKGROUND

Dementia, especially dementia caused by Alzheimer's disease, is considered one of the most important health problems of our time. This is because of the growing number of people affected by the disease, around 50 million currently in the world, as well as the suffering that it causes, not only to the affected patient but also to their family. Furthermore, the disease puts enormous strain on health, social health and economic resources, which are expected to grow in the future in part as a result of population ageing.

It is currently known that the disease begins many years before it manifests as clinical symptoms, and early diagnosis of the disease is desirable. In general, the sooner early signs of cognitive impairment are detected, the more we are able to prevent further deterioration. Detection of cognitive impairments such as dementia is an area of active research.

It is therefore generally desirable to be able to detect early signs of cognitive impairment. At present, in order to detect cognitive impairment, a patient would attend a consultation with a clinical practitioner. During the consultation, the clinical practitioner would typically ask the patient to complete a few neuropsychological tests, usually involving asking the patient to make verbal responses to some standard questions. An array of known neuropsychological tests exist, and have been used as standard practice for the past two to three decades. The neuropsychological tests may result in a number of scores, which may be added up to a final score. The final score may fall within one of several ranges, which may be used by the clinical practitioner to arrive at a diagnosis of the degree, if any, of cognitive impairment. The clinical practitioner may also make an overall assessment based subjective factors, and take that into account when making the diagnosis.

However, with a growing and ageing population, with limited health resources, it is often impractical to put a large number of at-risk patients through a consultation with a clinical practitioner. This is especially the case when the goal is to detect early signs of cognitive impairment, because a large section of the population may have some early signs of cognitive impairment which, to the untrained person, could appear to be normal behaviour associated with old age. As such, it may be desirable to improve the scalability of present screening methods for detecting cognitive impairment, particularly early signs of cognitive impairment.

In US 2018/0322894 A1, there is disclosed a method of detecting general medical conditions such as concussions (brain injury), Parkinson's disease or Alzheimer's disease. The method uses a mathematical model trained to diagnose a medical condition by processing acoustic features and language features of speech of a patient. As disclosed, the language features in question are speaking rate, number of pause fillers (e.g. "ums" and "ahs"), the difficulty of words, or the parts of speech of words following the pause fillers. However, while this method may provide some indication of general medical conditions, it is not particularly effective in providing reliable detection of cognitive impairment.

SUMMARY

Therefore, there exists a need for a scalable tool for accurate detection of cognitive impairment, especially early states of cognitive impairment.

The present invention is defined in the claims.

There is disclosed a computer-implemented method of detecting cognitive impairment. The method may comprise receiving audio data representing recorded utterances of a patient. The method may comprise processing the audio data using a speech-to-text engine to produce a text transcription of the recorded utterances. The method may comprise processing the text transcription to calculate a plurality of test variables associated with a neuropsychological test. The method may comprise calculating, by applying a trained detection model on the plurality of test variables, an impairment probability (511) indicating a likelihood that the patient suffers from the cognitive impairment. The method may comprise indicating that the patient suffers from the cognitive impairment if a final impairment probability based on the impairment probability is above a predetermined threshold, and indicating that the patient does not suffer from the cognitive impairment if the final impairment probability is below the predetermined threshold.

The neuropsychological test comprises any one of: a memory test (for example, CERAD or Digit Span), a semantic verbal fluency test, a phonetic verbal fluency test, an image description test, an open-subject spontaneous speech test, a paragraph reading test or are calling a memory from childhood test are examples of suitable tests.

The method may further comprise processing the text transcription to calculate a second plurality of test variables associated with a second neuropsychological test different from the first neuropsychological test. The method may comprise calculating, by applying a second trained detection model on the second plurality of test variables, a second impairment probability indicating a likelihood that the patient suffers from the cognitive impairment. The final impairment probability may be calculated based on the first and second impairment probabilities.

The second neuropsychological test may comprise a memory test or a semantic verbal fluency test.

The first and second neuropsychological tests may comprise, respectively, a memory test and a semantic verbal fluency test.

The method may further comprise processing the text transcription to calculate third and fourth pluralities of test variables associated respectively with third and fourth neuropsychological tests, wherein the first, second, third and fourth neuropsychological tests are all different from one another. The method may comprise calculating, by applying third and fourth trained detection models respectively to the third and fourth pluralities of test variables, third and fourth impairment probabilities, respectively, each indicating a likelihood that the patient suffers from the cognitive impairment. The final impairment probability may be calculated based on the first, second, third and fourth impairment probabilities.

The final impairment probability may be calculated using a trained final detection model.

Indicating that the patient suffers from the cognitive impairment may comprise indicating that the patient suffers from dementia if the final impairment probability is above a second predetermined threshold greater than the first predetermined threshold, and indicating that the patient suffers from mild cognitive impairment if the final impairment probability is between the first and second predetermined thresholds.

The memory test may be for measuring one, two or all of: immediate episodic verbal memory, learning ability, and delayed episodic verbal memory of the patient.

For measuring immediate episodic verbal memory, the plurality of test variables may comprise one, two or all of: number of correct words, percentage of incorrect words, and average correct word closeness. For measuring learning ability, the plurality of test variables may comprise one, two, or all of: mean number of correct words, mean percentage of incorrect words, and mean average correct word closeness. For measuring delayed episodic verbal memory, the plurality of test variables may comprise one, two or all of: answer accuracy percentage, answer recall percentage, and answer precision percentage.

The semantic verbal fluency test may be for measuring one, two, three or all of: counting fluency, clustering and switching fluency, prototypicality, and temporal clustering.

For measuring counting fluency, the plurality of test variables may comprise one or both of: number of animals, and percentage of time of silence. For measuring clustering and switching fluency, the plurality of test variables comprises one or both of: average animal cluster size, and average animal sub-cluster size. For measuring prototypicality, the plurality of test variables comprises one or both of: average prototypicality, and average prototypicality of first ten animals. For measuring temporal clustering, the plurality of test variables comprises one or both of: number of temporal clusters, and average temporal cluster size.

The method may further comprise processing the audio data using a trained acoustic model. The acoustic model may output an acoustic-based impairment probability indicating a likelihood that the patient suffers from the cognitive impairment. The final impairment probability may be calculated additionally based on the acoustic-based impairment probability.

The acoustic model may comprise a support vector machine.

The acoustic model may comprise extracting, from the audio data, a plurality of functionals according to AVEC 2013. The functionals may be selected using correlation-based feature selection.

The method may further comprise receiving personal information of the patient including at least one of age, gender, education level, place of birth, native language, and country of residence. The final impairment may be calculated additionally based on the personal information.

The method may further comprise, for each respective neuropsychological test, displaying predetermined visual information and/or providing predetermined audible information prompting the patient to complete the test by making utterances. The method may comprise generating the audio data by recording the utterances.

There is also disclosed a method of training a detection model for use in a neuropsychological test for detecting cognitive impairment of a patient, wherein the test comprises displaying predetermined visual information and/or providing predetermined audible information prompting the patient to complete the test by making utterances. The method may comprise, for each of a plurality of patients, conducting the neuropsychological test on the patient. The method may comprise, for each of a plurality of patients, receiving audio data representing recorded utterances made by the patient during the test. The method may comprise, for each of a plurality of patients, obtaining a diagnosis made by a clinical practitioner listening to the recorded utterances made by the patient. The method may comprise, for each of a plurality of patients, processing the audio data using a speech-to-text engine to produce a text transcription of the recorded utterances. The method may comprise, for each of a plurality of patients, processing the text transcription to calculate a plurality of test variables associated with a neuropsychological test. The method may comprise, for each of a plurality of patients, associating the plurality of test variables with the clinical practitioner's diagnosis for the patient. The method may comprise training the detection model using the pluralities of test variables and the plurality of associated diagnoses.

There is also disclosed a computer program product comprising instructions which, when the program is executed by one or more processors, cause the one or more processors to carry out the above method.

There is also disclosed a computer program product comprising instructions which, when the program is executed by one or more processors, cause the one or more processors to receive a selection of one or more neuropsychological tests from an operator, and, based on the selection, selectively carry out the above method.

There is disclosed a system comprising a mobile device and a data processing apparatus. The mobile device may be configured to present, to the patient, for each respective neuropsychological test, predetermined visual information and/or predetermined audible information prompting the patient to complete the test by making utterances. The mobile device may be configured to generate the audio data by recording the utterances. The mobile device may be configured to transmit the audio data to the data processing apparatus. The data processing apparatus may be configured to perform the above method.

The data processing apparatus may be a remote server.

The data processing apparatus may be another mobile device.

FIGURES

The invention will be described further below with reference to exemplary embodiments and the accompanying drawings, in which.

In the drawings, like parts are indicated by like reference numerals.

DETAILED DESCRIPTION

The present disclosure relates to detection of cognitive impairment of a patient using computer-implemented means. Broadly speaking, the patient is required to complete a neuropsychological test, during which the patient makes a number of utterances. The utterances may be recorded and processed by the computer-implemented means including applying one or more trained detection models, so as to make an indication of whether the patient suffers from cognitive impairment. In particular, the detection models may employ machine learning techniques. The approach of the present disclosure may enable scalable and accurate screening of cognitive impairment, which may be useful for large-scale screening for early signs of cognitive impairment.

Accordingly, there are disclosed a computer-implemented method of detecting cognitive impairment, a method of training a detection model for use in a neuropsychological test for detecting cognitive impairment, a computer program product for carrying out the method of detecting cognitive impairment, and a system comprising a mobile device and a data processing apparatus for carrying out the method of detecting cognitive impairment. The method of detecting cognitive impairment may be suitable for use as a fast screening method.

Dementia is a broad category of brain diseases that cause a long-term and often gradual decrease in the ability to think and remember that is severe enough to affect daily functioning. The most common type of dementia is Alzheimer's disease. Other common types include vascular dementia, dementia with Lewy bodies, and frontotemporal dementia. More than one type of dementia may exist in the same person, in which case a diagnosis of mixed dementia may be made. Diagnosis is commonly based on history of the illness and cognitive testing.

In the first stages of dementia, signs and symptoms may be subtle. The earliest stage of dementia is called mild cognitive impairment (MCI). Patients diagnosed with MCI often later progress to dementia. In MCI, changes in the patient's brain have been happening for a long time, but symptoms are just beginning to appear. These problems, however, are not severe enough to affect independent daily functioning. If and when the symptoms become severe enough to affect the patient's ability to function in normal daily activities, this could be an indication that the patient suffers from dementia. A patient with MCI may have some memory trouble and trouble finding words, but they are capable of solving everyday problems and competently handling their life affairs.

In the present disclosure, the term "cognitive impairment" is used collectively to refer to varying degrees of impairment, including MCI and dementia.

Figure 1:
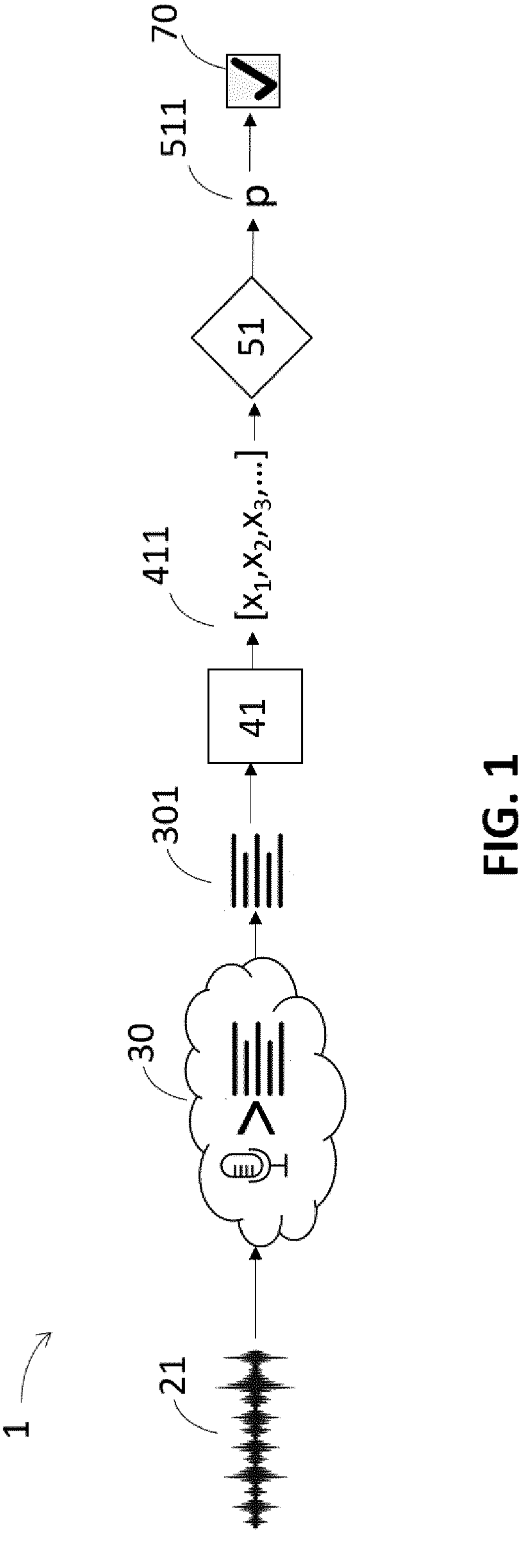
FIG. 1 depicts an arrangement for detecting cognitive impairment by processing received audio data according to a neuropsychological test.

In its broadest form, with reference to FIG. 1, the computer-implemented method of detecting cognitive impairment according to the present disclosure comprises: receiving audio data 21 representing recorded utterances of a patient; processing the audio data 21 using a speech-to-text engine 30 to produce a text transcription 301 of the recorded utterances; processing the text transcription 301 to calculate 41 a plurality of test variables 411 associated with a neuropsychological test; calculating, by applying a trained detection model 51 on the plurality of test variables 411, an impairment probability 511 indicating a likelihood that the patient suffers from the cognitive impairment; and indicating that the patient suffers from the cognitive impairment if a final impairment probability based on the impairment probability is above a predetermined threshold, and indicating that the patient does not suffer from the cognitive impairment if the final impairment probability is below the predetermined threshold.

In order to obtain the audio data 21, the patient may be prompted to make certain utterances. For example, the patient may be visually or audibly presented with a neuropsychological test, according to which the patient is required to say certain words or phrases. These words or phrases, or more generally utterances, may be recorded. The utterances may be recorded in electronic from, such as in an audio file stored on a computer, a mobile device or any computer-readable medium such as memory sticks or optical discs.

As a first step, audio data 21 representing the recorded utterances is received. Different ways of receiving the audio data 21 are possible. For example, audio data 21 stored on a memory stick or an optical disk may be inserted into a computer executing the method and transferred onto the computer. Alternatively, the computer executing the method may receive the audio data 21 from an external source, such as via a wired connection or via the internet. For another example, the device executing the method may be the same device that records the utterances of the patient, and so the audio data 21 representing the recorded utterances may be transferred internally within the device to the processor for subsequent processing.

The received audio data 21 may then be processed by a speech-to-text engine 30 to produce a text transcription 301 of the recorded utterances. The speech-to-text engine 30 may be implemented locally or remotely in an external server. Any suitable speech-to-text engine 30 may be used with the present method. For example, several speech-to-text 30 which are openly available on the market may be adapted for use with the present method. The raw output of the speech-to-text engine 30 may be used as is, or may be subjected to certain processing. For example, any non-words may be detected and removed from the raw output to produce the text transcription 301.

The audio data 21 may be passed to the speech-to-text engine 30 in its raw from, or may be subject to pre-processing. For example, background noise or echoes may be removed from the audio data before being processed by the speech-to-text engine 30, thereby improving the accuracy of the transcription and hence the outcome of the present method.

The text transcription 301 may be a simple string of text or may comprise other metadata. For example, the text transcription 301 may comprise temporal information, such as timestamps associated with different words in the text transcription 301. The inclusion of temporal information may be useful for certain neuropsychological tests which include temporal data as input.

Next, the text transcription 301 of the recorded utterances may be processed to calculate 41 a plurality of test variables 411. The plurality of test variables 411 may be associated with a neuropsychological test. That is, the plurality of test variables 411 may be chosen so that, when they are calculated from the text transcription 301, which is in turn obtained from recorded utterances made by a patient for a particular neuropsychological test, to be effective for use as input to a trained detection model 51 to calculate an impairment probability 511. The plurality of test variables 411 do not necessarily correspond to quantities or qualities that would be recorded by a clinician for the same neuropsychological test conducted in a conventional clinical setting, although for some tests they may happen to correspond. As will be discussed in more detail below, a number of available neuropsychological tests may be used. The test variables 411 may represent different features extracted from the text transcription 301, and the features extracted may depend on which neuropsychological test is being performed. Each of the plurality of test variables 411 may be a real number, and integer or a Boolean. Therefore, the plurality of test variables 411 may be collectively thought of as a vector or array of values.

The plurality of test variables 411 may be passed on to a trained detection model 51. The trained detection model 51, taking the plurality of test variables 411 as input, may calculate an impairment possibility 511 indicating a likelihood that the patient suffers from the cognitive impairment. The impairment possibility 511 may be represented by a real number or an integer or a Boolean. Although it is common in scientific fields for probability values to lie somewhere between 0 and 1, it should be understood that any other suitable numerical scales can be used as long as the likelihood of cognitive impairment can be represented. For example, the impairment probability may be measured between 0 and 100, or between −10 and +10. The scale may also be inverted, so that a high value may indicate low probability of impairment, and a low value may indicate high probability of impairment. The impairment possibility 511 may be used directly as the final impairment probability, or may be subjected to further calculations before arriving at the final impairment probability.

The use of a trained detection model 51 may result in an improved accuracy. For example, in conventional clinical or research settings, a point-based calculation may be used to process the test variables. For example, according to the conventional mini-mental state examination (MMSE), the patient is asked to respond to a list of questions, and a number of points is assigned for each question. The points are then added up to produce a final score ranging from 0 to 30. The range of 0 to 30 points may be divided into several sub-ranges corresponding to different severities of cognitive impairment ranging from no impairment to MCI to late-stage dementia. As can be seen, because the points are simply added up, any interrelational effects between the different questions are, in effect, not taken into account.

In other words, treating the points awarded for each question as different multidimensional data points, the approach in conventional questionnaire-type methods is equivalent to classifying the data points using a linear classifier, which performs poorly if the data points are not linearly separable in the data space. By contrast, using a trained detection model may allow interrelational effects between different test variables to be taken into account, and the impairment probability calculated by the detection model may encapsulate a non-linear classification of a set multi-dimensional data points comprising the test variables. As such, comparing like-for-like with conventional questionnaire-type methods based on a certain set of variables, the present method may be able to produce more accurate results by taking into account non-linear interrelational effects between the same test variables associated with a given neuropsychological test.

To determine whether the patient suffers from the cognitive impairment, a predetermined threshold may be applied. Specifically, the present method may indicate that the patient suffers from the cognitive impairment if the final impairment probability is above the predetermined threshold. Otherwise, if the final impairment probability is below the predetermined threshold, the present method may indicate that the patient does not suffer from the cognitive impairment, or may indicate that the patient is healthy. The indication 70 may be a binary indication, e.g. the patient either suffers from the cognitive impairment or the patient does not suffer from the cognitive impairment. As noted above, the term "cognitive impairment" may encompass varying degrees of impairment. Therefore, an indication 70 that the patient suffers from cognitive impairment may be subdivided into varying degrees of impairment.

As mentioned above, a range of neuropsychological tests may be used with the present method. Any scientifically-proven neuropsychological tests may be used, particularly those which have been used over the past two to three decades by clinical practitioners for diagnosing MCI and dementia. Tests which require the patient to speak or make utterances may be used, as the utterances can be recorded and represented as audio data 21. The audio data 21 may contain all the necessary information for arriving at an indication 70. This means that the audio data 21, if used instead in a conventional clinical setting, may contain all the necessary information for a clinical practitioner to arrive at a diagnosis. Therefore, using the same information, a trained detection model 51 may be able to compute an impairment probability 511. The following are some examples of suitable tests.

- Memory test: the CERAD (Consortium to Establish a Registry for Alzheimer's Disease) test may be used. During a session, the patient is asked to do the following. First, a series of words (e.g. 10 words) is presented to the patient. Later, at different moments during the session, the patient is asked to verbally repeat as many of the words as they can remember. Different phases of the test may be interleaved between other tests. Different cognitive functions can be measured by asking the patient to repeat the words at different moments during the session. The first, second and third time the patient is asked, the cognitive function being measured are, respectively, immediate episodic verbal memory, learning ability, and delayed episodic verbal memory. Finally, a larger series of words (e.g. 20 words) are successively presented to the patient, who has to answer "yes" or "no" depending on whether they believe the word is present in the original, smaller series of words. The number of correct answers may provide a further measurement of delayed episodic verbal memory.
- Memory test: the Digit Span test may be used. During the test, a series of numbers are presented to the patient, and the patient is asked to repeat it. The test starts with asking the patient to repeat a series of two numbers, and then to repeat a series of three numbers, and then to repeat a series of four numbers, etc. The test finishes when the patient fails to repeat a series. The Digit Span test may include two subtests: forward span (the patient is asked to repeat the series in the same order) and backward span (the patient is asked to repeat the series in reverse order).

Semantic verbal fluency test: The patient is asked to name as many examples from a category (e.g. animals) as the they can think of, within a certain time limit, e.g. 60 seconds. This test may provide a measurement of the semantic verbal fluency cognitive function. In particular, the cognitive function may be measured by test variables from the following categories: counting, clustering & switching, prototypicality, and temporal clustering.

Phonetic verbal fluency test: The patient is asked to say as many words starting with a certain consonant (e.g. letter F) as the patient can think of, within a certain time limit, e.g. 60 seconds. This test may provide a measurement of the phonetic verbal fluency cognitive function.

Image description test: A simple drawing is presented to the patient. For example, in the "Cookie Theft" test, a black-and-white simple drawing of a mother in a kitchen with two kids (and a series of details around the room and window) is presented to the patient. Any other simple drawing may be used. Then, the patient is asked to describe as many things as they can see in the picture, within a certain time limit, e.g. 90 seconds. The cognitive function being measured is oral verbal expression.

Open-subject spontaneous speech test: An open-subject question, conversation or topic is presented to the patient. For example, the patient may be asked to tell something positive that has happened to him/her in the last week. Then, the patient is asked to speak about it within a certain time limit, e.g. 90 seconds. The cognitive function being measured is oral verbal expression.

Recalling a memory from childhood test: The patient is asked to remember something from his/her childhood and speak about it within a certain time limit, e.g. 90 seconds. The cognitive function being measured is oral verbal expression.

Paragraph reading test: The patient is presented with a short paragraph or story, which he/she is asked to read. Then, the patient is asked several questions about it. For example, the patient may be asked what the paragraph is about. The cognitive functions being measured is oral verbal expression and reading comprehension.

A second neuropsychological test may be used in addition to the first neuropsychological test. The second neuropsychological test may be different from the first neuropsychological test. One or both of the first and second neuropsychological tests may be chosen from the list of neuropsychological tests disclosed in the present application. The text transcription 301 of the recorded utterances may be processed to calculate 42 a second plurality of test variables 421 associated with the second neuropsychological test 42. The audio data 21, and hence the text transcription 301, may be organised in sections corresponding to different neuropsychological tests. In this case, the processing of the text transcription 301 for each of the first and second neuropsychological tests may use only the relevant section of the text transcription 301. Alternatively, a section of the text transcription 301, or the entire text transcription 301, may be used as input to calculate 41, 42 each of the pluralities of test variables 411, 421 associated respectively with the first and second neuropsychological tests. In order to determine the starting point and the end point of a particular section of the text transcription 301, the temporal metadata associated with the text transcription 301 may be used. For example, during a performance of the present method, the start time and end time of each section of the audio data 21 corresponding to the respective neuropsychological test may be recorded and, using the temporal metadata associated with the text transcription 301, different sections of the text transcription 301 may be distinguished.

Figure 2:
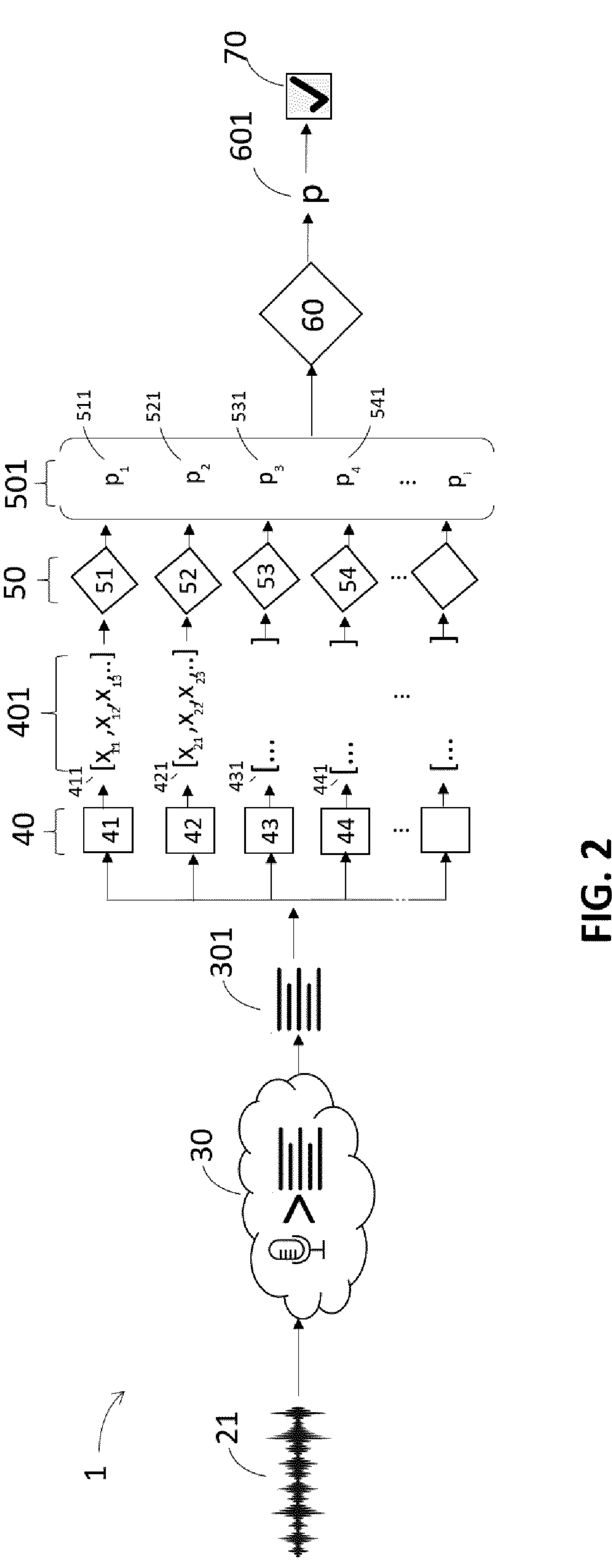
FIG. 2 depicts an arrangement for detecting cognitive impairment by processing received audio data according to several neuropsychological tests.

With reference to FIG. 2, using the second plurality of test variables 421 as input, a second trained detection model 52 may be used to calculate a second impairment probability 521 indicating a likelihood that a patient suffers from the cognitive impairment. The arrangement of the second plurality of test variables 421 and the calculation 42 thereof, the second trained detection model 52 and the second impairment probability 521 may be similar to the arrangement of the first plurality of test variables 411 and the calculation 41 thereof, the first trained detection model 51, and the first impairment probability 511, except that the second plurality of test variables 421 is associated with a different neuropsychological test. That is, the second plurality of test variables 421 may be chosen so that, when they are calculated from the text transcription 301, which is in turn obtained in part from recorded utterances made by a patient for the second neuropsychological test, to be effective for use as input to the second trained detection model 52 to calculate a second impairment probability 521.

As shown in FIG. 2, by processing the text transcription 301 using the appropriate calculations 41, 42, first and second impairment probabilities 511, 521 may be obtained. The first and second impairment probabilities 511, 521 may be collectively thought of as a probability vector 501. A final impairment 601 may be calculated based on the first and second impairment probabilities 511, 521. Using the final impairment probability 601, an indication 70 as to whether the patient suffers from the cognitive impairment can be produced. As noted above, a positive or negative indication 70 may depend on whether the final impairment probability 601 is above or below a predetermined threshold.

As found by the present inventors, the following two neuropsychological tests are particularly suited to the present method, namely the memory test and the semantic verbal fluency test. These tests are found to produce particularly good performance (the meaning of "good performance" will be discussed below). As such, where the method uses two or more neuropsychological tests, one of the neuropsychological tests may comprise a memory test or a semantic verbal fluency test. Optionally, the first and second neuropsychological tests may comprise, respectively, the memory test and the semantic verbal fluency test.

As noted above, the text description 301 may be processed to calculate 41, 42 first and second pluralities of test variables 411, 421 associated with first and second neuropsychological tests, and first and second impairment probabilities 511, 521 may be calculated by first and second trained detection models 51, 52. The present method may further comprise processing the text transcription 301 to calculate 43 a third plurality of test variables 431 associated with a third neuropsychological test. A third impairment probability 531 may be calculated by applying a third detection model 53 on the third plurality of test variables. The final impairment probability 601 may be calculated based on the first, second and third impairment probabilities 511, 521, 531, and an indication 70 of whether this patient suffers from the cognitive impairment may be produced based on the final impairment probability 601.

In addition to the third neuropsychological test and the third trained detection model 53, the present method may implement a fourth neuropsychological test and a corresponding fourth trained detection model 54. The text transcription 301 may additionally be processed to calculate a fourth plurality of test variables 441 associated with the fourth neuropsychological test 44. A fourth impairment probability 541 may be calculated by a fourth trained detection model 54 based on the fourth plurality of test variables 441 as input variables. The final impairment probability 601 may be calculated additionally based on the fourth impairment probability 541. That is, the final impairment probability 601 may be calculated based on the first, second, third and fourth impairment probabilities 511, 521, 531, 541, and an indication 70 may be produced based on the final impairment probability. The impairment probabilities 511, 521, 531, 541 may be collectively thought of as a plurality of impairment probabilities 501.

As shown in FIG. 2, test variables associated with further neuropsychological tests may be calculated and trained detection models beyond the fourth may be used to calculate additional impairment probabilities, and the final impairment probability 601 may be calculated additionally based on any such additional impairment probabilities.

In other words, in general terms, the text transcription 301 may be processed to calculate 40 pluralities of test variables 401 associated with a plurality of neuropsychological tests. As noted above, the audio data 21, and hence the text transcription 301, may be organised in sections corresponding to each of the plurality of neuropsychological tests. The processing of the text transcription 301 for each of the plurality of neuropsychological tests may use only the relevant section of the text transcription 301. Alternatively, a section of the text transcription 301, or the entire text transcription 301, may be used in feature extraction associated with any number of the plurality of neuropsychological tests. In order to determine the starting point and the end point of a particular section of the text transcription 301, the temporal metadata associated with the text transcription 301 may be used as disclosed above. Alternatively, different sections of the text transcription 301 may be stored as separate audio files. A corresponding plurality of trained detection models 50 may take the respective pluralities of test variables to calculate an impairment probability, resulting in a plurality of impairment probabilities 501. Using the plurality of impairment probabilities 501, the final impairment probability 601 may be calculated and an indication 70 may be provided.

As shown in FIG. 2, each of the detection models 51, 52, 53, 54 may take only the corresponding plurality of test variables 411, 421, 431, 441 as input. In such an arrangement, each detection model 51, 52, 53, 54 may be trained individually using the plurality of test variables 411, 421, 431, 441 associated with a neuropsychological test.

Alternatively, although not shown in FIG. 2, any of the detection models 51, 52, 53, 54 may take test variables associated with one or more other neuropsychological tests as input. For example, the first detection model 51 may take any or all of the second, third and fourth pluralities of test variables 421, 431, 441 in addition to the first plurality of test variables 411 as input, so as to calculate the first impairment probability 511. By using more test variables as input, the detection models 51, 52, 53, 54 may be able to calculate impairment probabilities 511, 521, 531, 541 with greater accuracy. In this arrangement, it is to be understood that the relevant detection model 51, 52, 53, 54 should be trained with test variables additional to those associated with the respective neuropsychological test.

As mentioned above, the final impairment probability 601 may be calculated based on a plurality of impairment probabilities 501 comprising any number of impairment probabilities 511, 521, 531, 541. Taking the plurality of impairment probabilities 501 as input, the final impairment probability 601 may be calculated by a trained final detection model 60. By using a trained final detection model 60 to calculate the final impairment probability 601 based on the plurality of impairment probabilities 501, any interrelational effects between the impairment probabilities 511, 521, 531, 541 may be taken into account by the final detection model 60. Alternatively or additionally, the trained final detection model 60 may calculate the final impairment probability 601 using one or more of the test variables from the pluralities of test variables 411, 421, 431, 441 directly as input, or as input in addition to any number of impairment probabilities 511, 521, 531, 541. The final impairment probability 601 may be calculated using other strategies, such as majority voting or weighted average. As such, the final impairment probability 601 calculated in this way may be more accurate than if, for example, the impairment probabilities 511, 521, 531, 541, were simply added together as a linear weighted sum.

As noted above, the indication 70, calculated based on the final impairment probability 601, may be a binary indication indicating whether or not the patient suffers from the cognitive impairment. As mentioned above, an indication 70 of cognitive impairment may be subdivided into varying degrees of impairment. For example, the indication 70 may indicate one of three possible outcomes, which may be 1) no cognitive impairment, 2) mild cognitive impairment, and 3) dementia. In this case, two predetermined thresholds may be used. In other words, a final impairment probability 601 below the first predetermined threshold may result in an indication 70 of no cognitive impairment. A second predetermined threshold greater than the first predetermine threshold may be defined. A final impairment probability 601 greater than the second predetermined threshold may result in an indication 70 of dementia. A final impairment threshold 601 falling between the first and second predetermined may result in an indication 70 of MCI.

As such, by dividing the final impairment probability 601 into three ranges using two predetermined thresholds, the indication 70 may indicate an absence of impairment or one of two degrees of impairment. It should be understood that a finer division of the ranges of final impairment probability 601 may be used. That is, three or more predetermined thresholds may be defined and applied to the final impairment probability 601, so that the indication 70 may indicate four or more possible outcomes corresponding to varying degrees of cognitive impairment or non-impairment.

In some applications, it may be useful, from a health policy point of view, to provide fast and effective screening of mild cognitive impairment or early stage dementia. In this case, it may be enough to use two predetermined thresholds resulting in three possible outcomes, namely 1) no cognitive impairment, 2) mild cognitive impairment, and 3) dementia.

As mentioned above, the memory test may be capable of measuring intermediate episodic verbal memory, learning ability, and delayed episodic verbal memory of the patient. Depending on the cognitive function to be measured, the memory test may be adapted for measuring one, two or all of these cognitive functions. By measuring a greater number of these cognitive functions, a more accurate indication 70 may be obtainable. Conversely, by measuring a smaller number of these cognitive functions, the patient may be able to complete the test in a shorter time, thereby allowing more patients to be screened using the same resources. This may be useful for screening a large number of patients for early MCI. Furthermore, less computing resources may be required, and/or the indication 70 may take less time to compute.

Similarly, as mentioned above, the semantic verbal fluency test may be capable of measuring counting fluency, clustering and switching fluency, prototypicality, and temporal clustering. For the present method, depending on the cognitive function or functions to be measured one, two, three or all of these cognitive functions may be measured.

In order to measure the cognitive functions associated with each of the neuropsychological tests mentioned above, a number of features may be extracted from the text transcription 301. To facilitate feature extraction, the text transcription 301 may be transformed into a tree-like structure as part of the processing step to calculate a plurality of test variables 411, 421, 431, 441. A tree-like structure may allow different features to be constructed by manipulating the tree-like data.

For example, as mentioned above, the memory test may involve presenting a number of words to the patient, and asking the patient to immediately repeat the words. For the measurement of intermediate episodic verbal memory, the number of words correctly repeated by the patient may be counted. With the present invention, using the text transcription 301, the words uttered by the patient may be conveniently compared with the words originally presented to the patient, which are determined in advance. Accordingly, one of the test variables associated with the memory test may be the number of correct words repeated by the patient immediately after the words were presented to the patient.

Detailed descriptions of the clinical practice of the neuropsychological tests and the associated test variables may be found in references 5-9 listed at the end of the description: memory test (reference 5), semantic verbal fluency test (reference 6: clustering & switching; reference 7: counting; reference 8: temporal clustering), image description test (reference 9), and phonetic verbal fluency test (reference 7).

As described in these documents, a wide range of test variables may be extracted. However, as found by the present inventors, when applied to the present method, certain test variables may provide better predictive power than other possible test variables. Furthermore, certain pairs of test variables may be inherently closely correlated with each other and, as such, using both test variables may provide little additional predictive power over using just one of the two test variables in the correlated pair. It may be desirable to choose test variables which, individually, provides significant predictive power. As well as allowing the patient to complete the test in a shorter time, thereby allowing more patients to be screened using the same resources, choosing test variables this way may allow a high degree of accuracy to be preserved despite a reduction in the number of test variables used. This may be useful for accurately screening a large number of patients for early MCI. Furthermore, by using a relative small number of test variables, it may be easier for operators and clinicians to appreciate how each variable might be affecting the result and thereby establish a level of trust of the present method.

Through extensive research, the following list of test variables are found to be suitable:

- Memory test (see reference 5):
  - Immediate episodic verbal memory
    - Number of correct words
    - % of incorrect words
    - Average correct word closeness, i.e. the average position of the correct words. In a test where a series of (e.g. 10) words are presented, this variable measures whether the patient remembers the words early in the series more, or those later in the series more, or remembers them uniformly.
  - Learning ability
    - Mean number of correct words, i.e. the mean number of correct words amongst the patient's attempted repetitions of the words at different moments during the session.
    - Mean % of incorrect words, i.e. the mean % of incorrect words amongst the patient's attempted repetitions of the words at different moments during the session.
    - Mean average correct word closeness, i.e. the mean of the average correct word closeness amongst the patient's attempted repetitions the words at different moments during the session.
  - Delayed episodic verbal memory
    - % patient's answer accuracy, i.e. the number of correct words divided by the total number of words
    - % patient's answer recall, i.e. the number of words correctly identified by the patient as being in the original list, divided by the total number of words in the original list
    - % patient's answer precision, i.e. the number of words correctly identified by the patient as being in the original list, divided by the total number of words identified (correctly or incorrectly) by the patient as being in the original list
- Semantic verbal fluency test:
  - Counting (see reference 7)
    - Number of animals
    - % of seconds in silence
  - Clustering & switching (see reference 6)
    - Average animal cluster size: A sub-cluster is a series of consecutive animals named by the patient that belong to a certain sub-type. This variable measures the average number of animals within sub-clusters
    - Average animal sub-cluster size: A cluster is a series of consecutive animals named by the patient that belong to a certain type. This variable measures the average number of animals within clusters
  - Prototypicality
    - Average prototypicality: The prototypicality of an animal measures whether the animal is common or rare. This variable measures the average prototypicality of animals said by the patient
    - Average prototypicality first 10 animals: Average prototypicality of first 10 animals said by the patient
  - Temporal clustering (see reference 8)
    - Number of temporal clusters: A temporal cluster is an aggregation of animals within time. This variable measures the number of temporal clusters
    - Average temporal cluster size: Average number of animals within temporal clusters Image description test (see reference 9):

Counting

Number of nouns

Number of verbs

Ratio nouns/pronouns

Phonetic verbal fluency test:

Counting

Number of correct F-words

% of incorrect words

% of seconds in silence

As part of a trade-off between speed and accuracy of the indication 70, any number of the neuropsychological tests, such as those listed above, may be implemented. Within the memory test of the semantic verbal fluency test, any number of the cognitive functions listed above may be implemented. Furthermore, within each of the cognitive functions listed above, any number of test variables may be extracted from the text transcription 301.

In other words, in the memory test, for measuring immediate episodic verbal memory, the plurality of test variables may comprise one, two or all of: number of correct words, percentage of incorrect words, and average correct word closeness; for measuring learning ability, the plurality of test variables may comprise one, two, or all of: mean number of correct words, mean percentage of incorrect words, and mean average correct word closeness; for measuring delayed episodic verbal memory, the plurality of test variables may comprise one, two or all of: answer accuracy percentage, answer recall percentage, and answer precision percentage.

In the semantic verbal fluency test, for measuring counting fluency, the plurality of test variables may comprise one or both of: number of animals, and percentage of time of silence; for measuring clustering and switching fluency, the plurality of test variables may comprise one or both of: average animal cluster size, and average animal sub-cluster size; for measuring prototypicality, the plurality of test variables may comprise one or both of: average prototypicality, and average prototypicality of first ten animals; for measuring temporal clustering, the plurality of test variables may comprise one or both of: number of temporal clusters, and average temporal cluster size.

In the image description test, for measuring the counting cognitive function, the plurality of test variables may include one, two or all of: number of nouns, number of verbs, and ratio of nouns/pronouns.

In the phonetic verbal fluency test, for measuring the counting cognitive function, the plurality of test variables may include one, two or all of: number of correct F-words, % of incorrect words, and % of seconds in silence.

Figure 3:
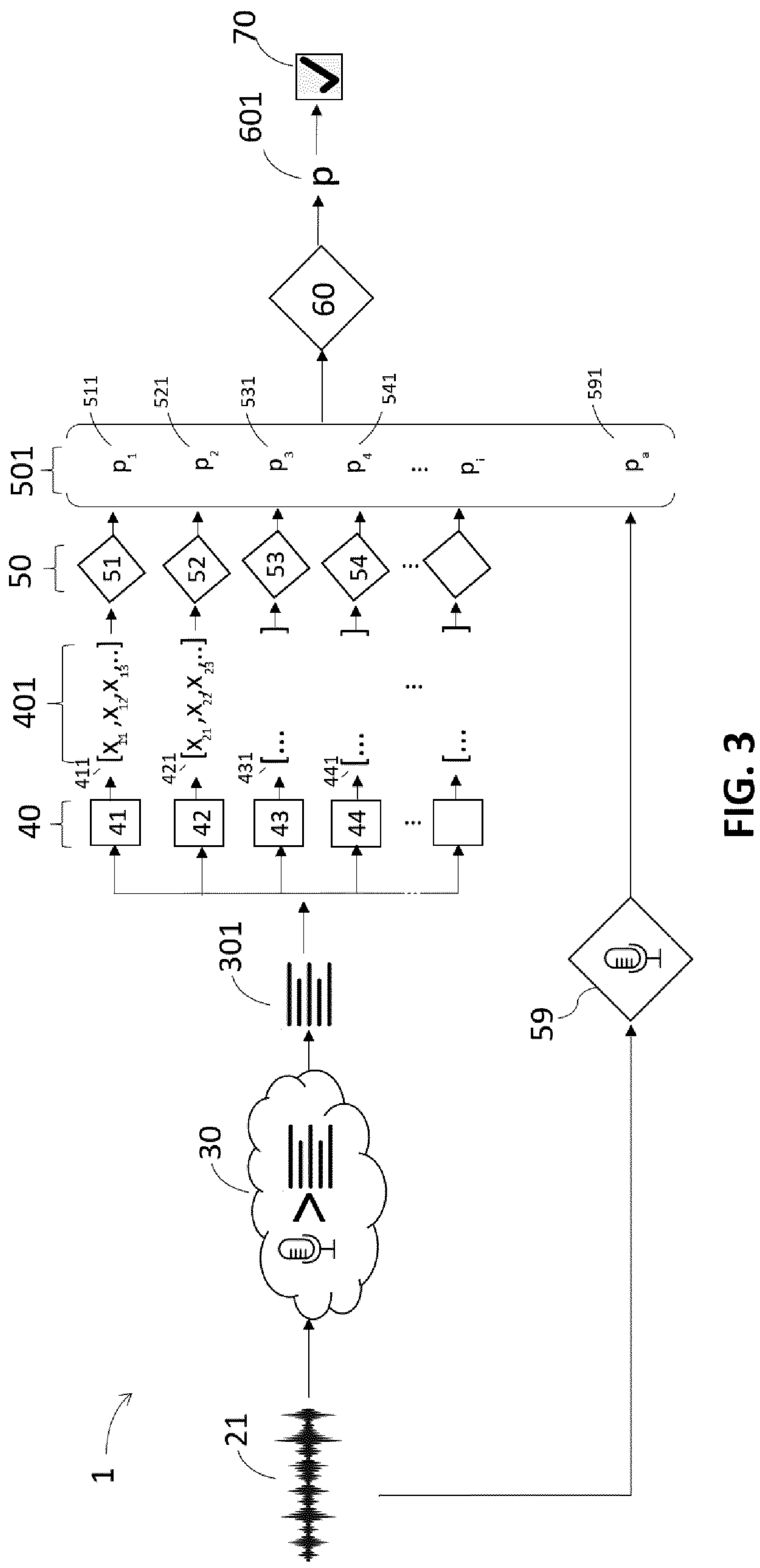
FIG. 3 depicts an arrangement for detecting cognitive impairment by processing received audio data according to one or more neuropsychological tests and an acoustic model.

With reference to FIG. 3, in addition to neuropsychological tests, the present method may comprise processing the audio data 21 using an acoustic model 59 to calculate an acoustic-based impairment probability 591. As with the detection models 51, 52, 53, 54, the impairment probability 591 calculated by the acoustic model 59 may indicate a likelihood that the patient suffers from the cognitive impairment. As shown in FIG. 3, the audio data 21 may be passed on to the acoustic model 59 without going through a step of text transcription. In other words, the acoustic model may operate on acoustic features rather than semantic features.

As shown in FIG. 3, the audio data 21 used as input to the acoustic model 59 may be the same audio data 21 which is used to produce the text transcription 301. In other words, in order to calculate the acoustic based impairment probability 591, it may not be necessary to obtain a separate recording of the patient's utterances. Instead, the utterances made for the purpose of completing the neuropsychological tests may also be used for processing by the acoustic model 59. This is because the acoustic model 59 may be agnostic to the semantic content of the utterances.

Nevertheless, in order to make efficient use of computing resources, silences in the audio data 21 may be removed before the audio data 21 is passed on to the acoustic model 59. In general, if the audio data 21 is to contain utterances made by the patient for several different neuropsychological tests, there may be periods of silence in the audio data 21 because it may take the patient a certain length of time to move from one test to another. In particular, when a new test is presented to the patient, the patient may take time to understand what utterances they are being asked to make. Alternatively, the recording may be paused while the patient takes time to understand the test and/or moving from one test to another, thereby avoiding long sections of silence in the audio data 21. Nevertheless, at least for neuropsychological tests in which temporal information is unimportant, silences between utterances may be removed. To remove the silences, a voice activity detector (VAD) may be used. Where the audio data 21 is initially recorded as separate files, these may be concatenated into a single audio file.

By using acoustic-based processing, the accuracy of the indication 70 may be further improved. This is because there is broad scientific consensus that certain non-linguistic vocal characteristics can be good indicators of the mental condition and/or emotional state of a patient. These characteristics, which include prosody (fundamental frequency and speed of speech), spectral representations (Mel cepstra coefficients or PLP), articulation (frequencies of the vocal tract formants) and glottic excitation (temporal fluctuation, "shimmer" and aspiration level), may be measured by the acoustic model 59 so as to detect cognitive impairment.

For the acoustic model 59, a number of suitable models may be used. For example, the iVector system may be used. References 1 and 2 provide example implementations of the iVector system.

In general, in order to calculate the acoustic-based impairment probability 591 using iVectors, three audio processing blocks may be used, namely "front-end", "speech representation" and "classification".

The "front-end" may be the first block. In this block the audio data 21 is taken as input, and an analysis may be performed to obtain a set of 45 spectrum-related features (13 PLP+F0+Voicing together with delta and delta-delta). These characteristics may be extracted using a 25 millisecond sliding window and a 10 millisecond displacement. As such, each audio file after passing through this block may be represented by a set of vectors of dimension 45 ("acoustic features"), ordered temporally. The software Kaldi (see http://kaldi-asr.org/) may be used to implement this block.

A second block may be responsible for obtaining a representation of the audio from the acoustic characteristics obtained by the first block. "iVectors" may be used to make this representation. Instead of extracting an iVector to represent the entire audio data 21, the audio data 21 may be divided into pieces or segments of shorter duration, and therefore there may be several segments of audio for each patient (note that silences in the audio data 21 may have been removed already). Each of these segments may be represented or modeled by an iVector of a certain dimension that can be adjusted. As a result, after this block, a set of iVectors (as many iVectors as there are audio segments) may be obtained, which may then used in the third block (classification). To obtain the iVectors, two models UBM and T may be used, which must be previously trained. The UBM model may be trained with publicly available data, such as the voice corpus known as "Biosecure" (see reference 3). The software Kaldi may be used to implement this block.

A third block may be responsible for classifying the iVectors provided by the second block. As a classifier, an SVM (Support Vector Machine) with a linear kernel may be used. Since there may be several segments from the second block, and hence several iVectors for each patient, there may also be several classification results (one for each segment). The classification results may be combined together obtain the acoustic-based impairment probability 591.

In the second block (iVectors), various parameters that may be adjusted, such as the iVectors dimension and the size and displacement of the sliding window. For example, 200 dimensions for the iVectors (i.e. there are 200 parameters to represent each audio segment) and a 20-second window with a 5-second offset between consecutive windows may be used.

Instead of or in addition to iVectors, "functionals" according to the Audio-Visual Emotion and Depression Recognition Challenge 2013 (AVEC 2013) may be used to construct the acoustic model 59, details of which may be found in reference 4.

This AVEC 2013 functionals system is similar to the iVectors system, with the difference that, instead of representing the audio data 21 with a set of iVectors (one iVector per segment), the audio data 21 may be represented with a set of "functionals". These functionals may be extracted from a wide variety of acoustic characteristics, such as using the openSMILE software (see https://www.audeering.com/opensmile/). As a starting point, the "functionals" proposed in the AVEC 2013 evaluation (Audio-Visual Emotion and Depression Recognition Challenge) may be used, which consists of a set of 2268 available characteristics (functionals) extracted from 32 descriptors of bass level (low-level descriptors) of the audio signal related to energy, spectrum, loudness and pitch. The two tables below list some of the characteristics suitable for use with the present method.

TABLE 1

| 32 low level descriptors. |
|---|
| Energy & spectral (32) |
| loudness (auditory model based), zero crossing rate, energy in bands from 250-650 Hz, 1 kHz-4 kHz, 25%, 50%, 75% and 90% spectral roll-off points, spectral flux, entropy, variance, skewness, kurtosis, psychoacoustic sharpness, harmonicity, flatness, MFCC 1-16 |
| Voicing related (6) |
| $F_0$ (sub harmonic summation, followed by Viterbi smoothing), probability of voicing, jitter, shimmer (local), jitter (delta: "jitter of jitter"), logarithmic Harmonics-to-Noise Ratio (logHNR) |

TABLE 2

| Set of all 42 functionals. |
|---|
| Statistical functionals (23) |
| (positive[2]) arithmetic mean, root quadratic mean, standard deviation, flatness, skewness, kurtosis, quartiles, inter-quartile ranges, 1%, 99% percentile, percentile range 1%-99%, percentage of frames contour is above: minimum + 25%, 50%, and 90% of the range, percentage of frames contour is rising, maximum, mean, minimum segment length[1, 3], standard deviation of segment length[1, 3] |
| Regression functionals[1] (4) |
| linear regression slope, and corresponding approximation error (linear), quadratic regression coefficient a, and approximation error (linear) |
| Local minima/maxima related functionals[1] (9) |
| mean and standard deviation of rising and falling slopes (minimum to maximum), mean and standard deviation of inter-maxima distances, amplitude mean or maxima, amplitude range of minima, amplitude range of maxima |
| Other[1, 3] (6) |
| LP gain, LPC 1-5 |

[1]Not applied to delta coefficient contours.

[2]For delta coefficients the mean of only positive values is applied, otherwise the arithmetic mean is applied.

[3]Not applied to voicing related LLD

As in the iVector system, a segmentation strategy may be used with the AVEC 2013 functionals. Each segment may be represented using the selected functionals (up to 2268). As the number of characteristics can be very high in relation to the available training data, in order to avoid the so-called "curse of dimensionality" in the context of statistics and machine learning, a selection of those most representative functionals may be made. A correlation based feature selection algorithm may be used to select the most representative functionals. The WEKA software (see https:/www.cs.waikato.ac.nz/ml/weka/) may be used for this purpose.

Figure 4:
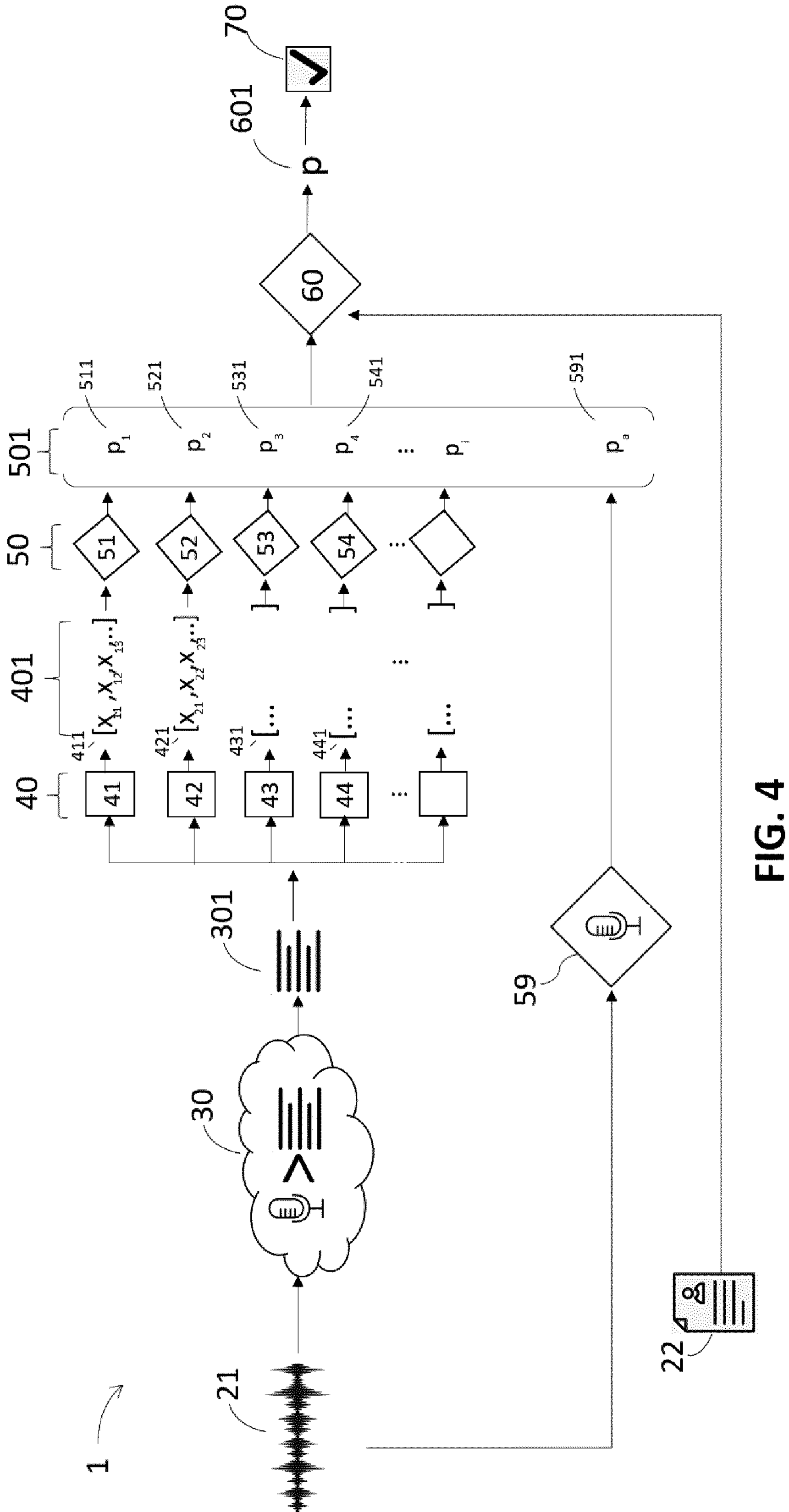
FIG. 4 depicts an arrangement for detecting cognitive impairment by processing received audio data according to one or more neuropsychological tests and, optionally, an acoustic model, and by processing personal information of the patient.

With reference to FIG. 4, in addition to the impairment probabilities 511, 521, 531, 541 associated with one or more neuropsychological tests, personal information 22 of the patient may be used as additional input to the calculation of the final impairment probability 601. As mentioned above, the acoustic model 59 may also be used. The personal information 22 may include any or all of age, gender, education level, place of birth, native language, and country of residence. Including personal information 22 in the calculation of the final impairment probability 601 may be useful because age, gender, education level, place of birth, native language, and country of residence may have a systemic influence on the impairment probabilities 511, 521, 531, 541 calculated from test variables 411, 421, 431, 441 associated with to neuropsychological tests, but which is not indicative of cognitive impairment. For example, men tend to name a lower average number of animals in the semantic verbal fluency test, independent of the degree of cognitive impairment. For example, old people might have some minor memory issues due only to ageing, and not necessarily due to any early-stage MCI. Information such as place of birth or country of residence may allow cultural differences to be compensated for. As such, by additionally using personal information 22, the accuracy of the final impairment probability 601 and that of the indication 70 may be improved.

As noted above, the calculation of the final impairment probability 601 may be performed using the trained final detection model 60. Each item of personal information 22, for example age, gender, education level, place of birth, native language, and country of residence may serve as additional input data to the final detection model 60.

Each of the detection models 51, 52, 53, 54 and the final detection model 60 may be implemented using any suitable Machine Learning algorithm. Machine Learning techniques may be used to train models based on test variables mentioned above. These techniques may include supervised, unsupervised or reinforcement learning algorithms. The method may further include applying transformations to test variables. For example, Logistic Regression, Support Vector Machine, Decision Trees, K-Nearest Neighbours, Naïve Bayes, Bayesian Networks, Multilayer Perceptron (MLP), Convolutional Neural Network (CNN), Recurrent Neural Network (RNN), Long Short-Term Memory network (LSTM), Transformer network or autoencoders may be used. Ensembling algorithms such as Random Forests, AdaBoost, Gradient Boosting or Majority Voting may also be used. In addition to Machine Learning algorithms, feature selection (such as Lasso or Recursive Feature Elimination), dimensionality reduction (such as Principal Component Analysis) or normalization techniques may also be used.

As mentioned above, the patient may be asked to make utterances in accordance with different neuropsychological tests, which utterances may be recorded to generate the audio data 21 used in subsequent processing. In order to prompt the patient to make these utterances, the present method may further comprise displaying predetermined visual information. The predetermined visual information may be specific to a given neuropsychological test.

For example, in a memory test, the predetermined visual information may include text explaining to the patient what the test entails, followed by a series of words (e.g. 10 words) for the patient to try to remember. The predetermined visual information for a memory test may include further text prompts asking the patient to repeat the series of words at a later point in time. As mentioned above, by prompting the patient to repeat the words at different times, different cognitive functions may be measured. The predetermined visual information may include, at a later point in time, explanation to the patient that a second series of words, larger than the initial series of words, will be displayed, and the patient is required to answer "yes" or "no" depending on whether a displayed word is present in the initial series of words, all followed by a sequential display of the second series of words. Depending on which cognitive functions are to be measured, the predetermined visual information for a memory test may include or exclude subsequent text prompts. For example, if only immediate episodic verbal memory is to be measured, the predetermined visual information may include only one text prompt, immediately after displaying an explanation of the test and the series of words. For another example, if learning ability is to be measured, then the predetermined visual information may include a text prompt, sometime after displaying the initial series of words, asking the patient to repeat the words.

For another example, in a semantic verbal fluency test, the predetermined visual information may include a text-based instruction asking the patient to name as many animals (or another category of things) as possible within a time limit. The predetermined visual information may include a countdown timer showing the amount of time left (e.g. in seconds) of the time limit. As disclosed above, the time limit may be 60 seconds.

For another example, in a phonetic verbal fluency test, the predetermined visual information may include a text-based instruction asking the patient to name as many words starting with letter F (or another consonant) as they can think of within a time limit. The predetermined visual information may include a countdown timer showing the amount of time left (e.g. in seconds) of the time limit. As disclosed above, the time limit may be 60 seconds.

For another example, in an image description text, the predetermined visual information may include an image, and text-based instruction asking the patient to describe as many things as they can see in the image within a time limit. The image may be any suitable image. For example, the image may be a simple drawing, such as a black-and-white drawing. The image may be a picture of a mother in a kitchen with two children, or any other suitable content, such as a series of details around a room and the window. The predetermined visual information may include a countdown timer showing the amount of time left (e.g. in seconds) of the time limit. As disclosed above, the time limit may be 60 seconds.

Alternatively or additionally, any text-based component of the predetermined visual information mentioned above may be given as audible information to the patient. That is, the present method may comprise producing predetermined audible information prompting the patient to complete the test by making utterances. The audible information may comprise verbal explanation of what a given neuropsychological test entails. The audible information may comprise e.g. the series of words to be remembered by the patient in a memory test. The predetermined audible information itself may comprise audio recordings prepared in advance for any given neuropsychological tests, or may comprise audio generated using a text-to-speech engine according to a predetermined script for any given neuropsychological tests.

In a single session, the patient may be prompted to complete a series of different neuropsychological tests. Accordingly, predetermined visual information for each of the series of tests may be displayed in order, and/or predetermined audible information may be provided. As noted above, for the memory test, depending on the cognitive functions to be measured, the patient may be prompted to repeat the initial series of words at later points in time. If a series of different neuropsychological tests are to be conducted, then the different prompts of the memory test may be interleaved with the other neuropsychological tests. For example, the session may begin with a memory test, including an initial prompt for the patient to repeat the series of words for measuring immediate episodic verbal memory, followed by a different neuropsychological test (e.g. a semantic verbal fluency test), followed by a second prompt of the memory test for measuring learning ability, followed by another neuropsychological test (e.g. an image description test), followed by a final prompt of the memory test for measuring delayed episodic verbal memory.

At the end of each neuropsychological test, the next neuropsychological test may be presented to the patient automatically. The next neuropsychological test may be presented immediately without delay, or a pause of a fixed duration may be included. The start of each neuropsychological test may be indicated visually or audibly, such as by a "beep". Alternatively, the next neuropsychological test may be presented under the control of the patient. For example, the patient may be required to press a button (a physical button or a virtual button displayed on a touchscreen) in order to proceed to the next neuropsychological test. Alternatively or additionally, the patient may be required to verbally confirm that they are ready to proceed to the next test. The patient's verbally confirmation may be obtained by listening for utterances made by the patient, and using a voice recognition engine to determine whether the utterances include a confirmation to proceed. For example, the patient may be asked visually or audibly whether they are ready for the next test, and the patient may be required to verbally say "yes" in order to proceed.

Figure 8:
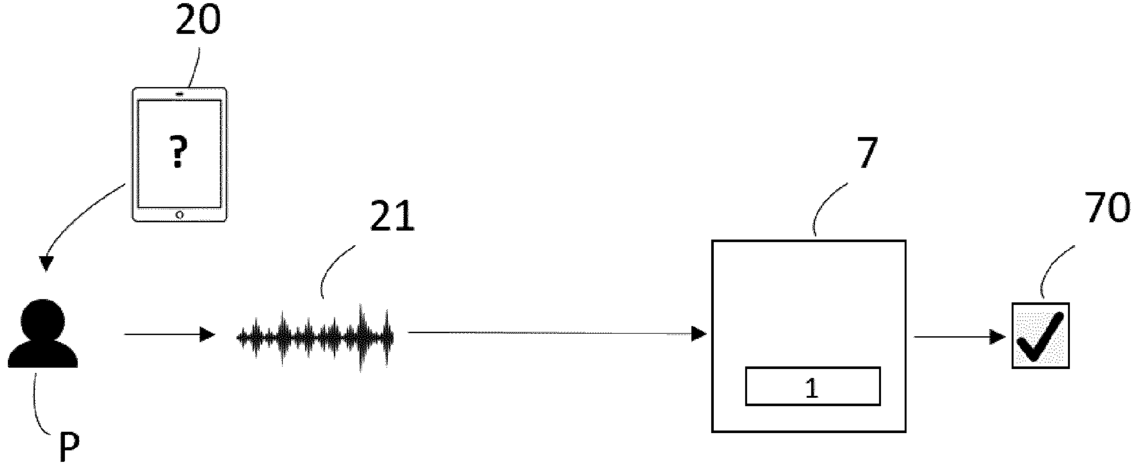
FIG. 8 depicts a system for executing the method of the present disclosure.

With reference to FIG. 8, the presentation of predetermined visual information and/or predetermined audio information may be achieved by a mobile device 20, which may be provided with a display and/or loudspeakers. The mobile device 20 may also record the utterances made by the patient P and generate audio data 21. For this purpose, the mobile device 20 may be provided with a microphone or an array of microphones. The mobile device 20 may transmit the audio data 21 to a data processing apparatus 7, and the data processing apparatus 7 may execute the present method from the point where audio data 21 is received. In other words, the present method may be executed by a system comprising the mobile device 20 and the data processing apparatus 7. Each of the mobile device 20 and the data processing apparatus 7 may have its own processor and memory.

The mobile device 20 may be connected to the data processing apparatus 7 by a direct wired connection, such as a USB connection or an Ethernet connection. Alternatively, the mobile device 20 may be connected to the data processing apparatus 7 by a local wireless connection, such as Bluetooth or Wi-Fi. Alternatively, the data processing apparatus 7 may be at a remote location away from the mobile device 20. For example, the data processing apparatus may be a remote server. In this case, the mobile device 20 may be connected to the data processing apparatus via a local area network (LAN), an intranet, or the internet. The mobile device 20 itself may be connected to the internet via a cellular telephone network. In all of these cases, the mobile device 20 may transmit the audio data 21 to the data processing apparatus 7 using the appropriate connection. Alternatively, the audio data 21 may be transferred from the mobile device 20 to a memory device first, such as a USB memory stick or an external hard drive, and then transferred from the memory device to the data processing apparatus 7. Instead of a typical server machine, the data processing apparatus 7 may itself be another mobile device. Furthermore, mobile device 20 may instead be a desktop computer or a fixed terminal connected to a website presenting and executing the neuropsychological tests. Mobile device 20 may also instead be a landline telephone connected to a landline network.

Figure 5:
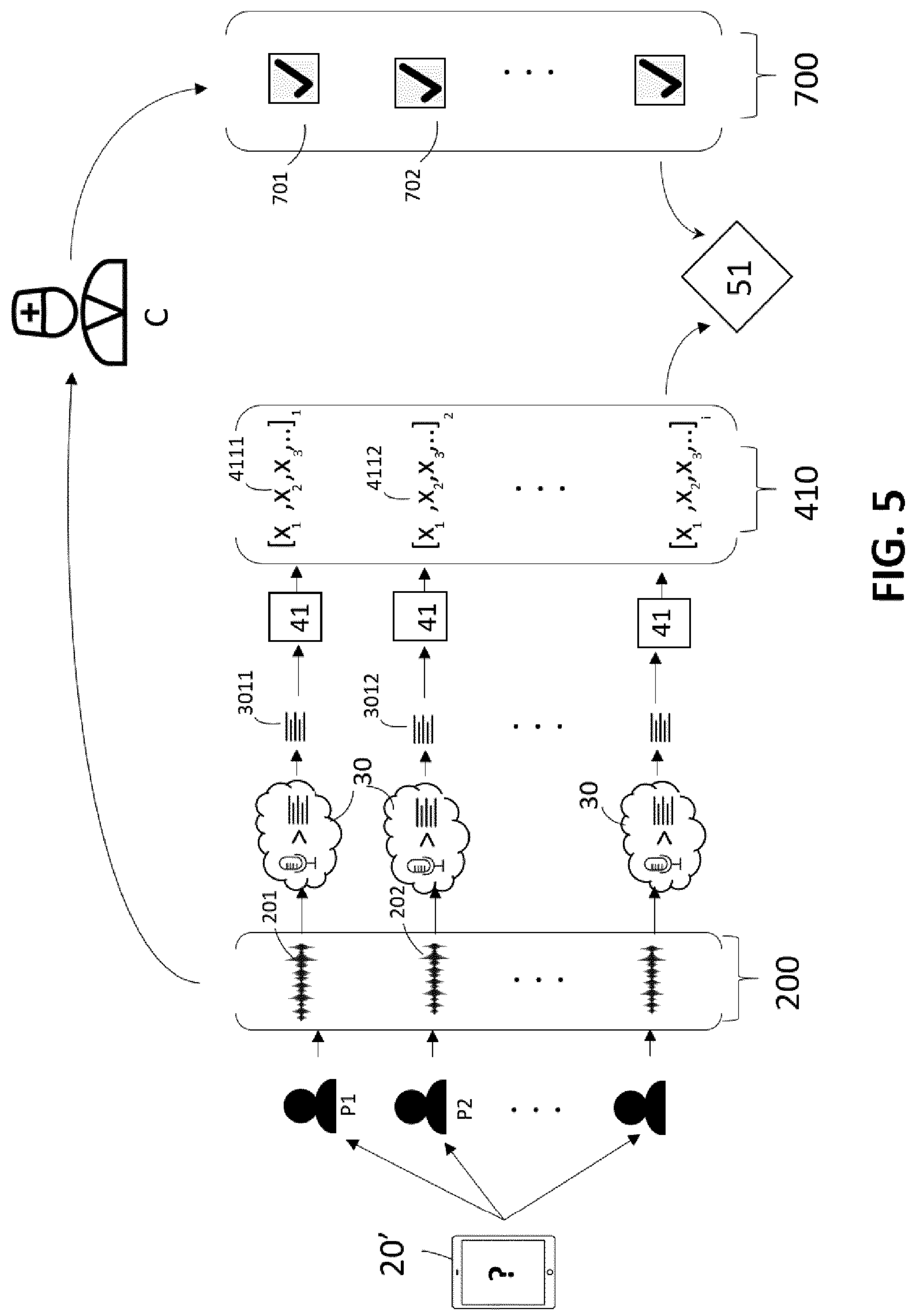
FIG. 5 depicts training a detection model for use in the detection of cognitive impairment.

As mentioned above, one or more detection models 51, 52, 53, 54 may be used in the present method. The detection models 51, 52, 53, 54 require prior training with reference data. Each of the detection models 51, 52, 53, 54 may be trained separately with its own set of reference data. With reference to FIG. 5, there is disclosed a method of training a detection model 51 for use with a neuropsychological test. It is to be understood that detection model 51 is being referred to for ease of reference only, and the same method can be used to train any of the other detection models 52, 53, 54 for use with a corresponding neuropsychological test.

As shown in FIG. 5, for a detection model 51 corresponding to a given neuropsychological test, a plurality of patients P1, P2 are required to complete the neuropsychological test. As in an actual performance of the method of detecting cognitive impairment disclosed in the present application, for the purpose of preparing training data, the neuropsychological test may also be presented to the patient P1, P2 by displaying predetermined visual information and/or providing predetermined audible information to the patient P1, P2 prompting them to make utterances. The test may be presented using a computing device 20'.

The utterances made by the patient P1, P2 during the test may be recorded, such as by the computing device 20'. The recorded utterances may be represented as audio data 201, 202 for the respective patient P1, P2. Analogous to the method of detecting cognitive impairment, the audio data 201, 202 may be received. Audio data 201, 202 may be collected from the plurality of patients P1, P2 to form a collection of audio data 200.

On one hand, the audio data 201, 202 may be given to a clinical practitioner C, who may listen to the recorded utterances represented by the audio data 201, 202. The clinical practitioner C may, based on the audio data 201, 202, make diagnoses 701, 702 indicating whether the respective patient P1, P2 suffers from the cognitive impairment. Each diagnosis 701, 702 may be associated with the respective patient P1, P2. The diagnoses 701, 702 may be binary, i.e. they may indicate whether the patient P1, P2 suffers from cognitive impairment or does not suffer from cognitive impairment. As noted above, the term "cognitive impairment" is used here collectively to indicate any degree of impairment, ranging from MCI to late-stage dementia. If it is desired to provide indications 70 which are more finely graduated, the clinical practitioner C may be asked to provide diagnoses indicating three possible outcomes: no cognitive impairment, MCI, or dementia. Finer graduation may be used as desired. In some applications, the method of detecting cognitive impairment may be intended primarily as a screening tool, and thus a simple binary indication 70 of no impairment vs impairment may be adequate.

On the other hand, analogous to the method of detecting cognitive impairment, the audio data 201, 202 may be processed by a speech-to-text engine 30 to produce respective text transcription 3011, 3012 of the recorded utterances made by the respective patient P1, P2. Analogous to the method of detecting cognitive impairment, the text transcription 3011, 3012 may be processed to calculate 41 a plurality of test variables 4111, 4112 associated with the respective neuropsychological test for which the detection model 51 is to be trained. At this point, each plurality of test variables 4111, 4112 may be associated with the respective diagnosis 701, 702 made by the clinical practitioner C. Each plurality of test variables 4111, 4112 may also be associated with the respective patient P1, P2.

As such, by repeating the above process for a plurality of patients P1, P2, a collection of pluralities of test variables 410 and a corresponding collection of diagnoses 700 may be obtained and may serve as reference data for training the detection model 51. The collection of diagnoses 700 may be taken as ground truth for the purpose of training the detection model 51. Using the collection of pluralities of test variables 410 and the corresponding collection of diagnoses 700, the detection model 51 may be trained.

For improved accuracy, the same collection of audio data 200 may be listened to by a second clinical practitioner or by several other clinical practitioners, and corresponding collections of diagnoses may be obtained. Since the several collections of diagnoses will be associated with the same collection of pluralities of test variables 410, in the training data for the detection model 51, the collection of pluralities of test variables 410 may be repeated as many times as there are collections of diagnoses. By using diagnoses made by several clinical practitioners, the quality of the "ground truth" may be improved compared with using diagnosis made by just one clinical practitioner C.

It is to be understood that, although FIG. 5 shows two patients P1, P2 for simplicity, the number of patients should be as large as resources allow. A sample size of 154 patients has been found to be enough for the method of detecting cognitive impairment to perform satisfactorily. It may be desirable for the sample size to be larger, for example in the order of thousands of patients.

The patients making up the samples may ideally comprise a mixture of people suffering from varying degrees of cognitive impairment as well as people who do not suffer from any cognitive impairment. For example, in a sample size of 154, a mixture of 81 people without impairment, 52 diagnosed with MCI and 21 diagnosed with dementia was found to provide suitable training data. The mixture of people may be balanced in terms of age and gender. The sample size of each population type (i.e., without impairment, with MCI and with dementia) should be such that populations are representative enough.

Using the training data, the detection model 51, 52, 53, 54 may be trained according to the following train-validation-test methodology. The methodology may be used, first, to train and select model parameters making up the detection model 51, 52, 53, 54, and, second, to test the detection model 51, 52, 53, 54 (i.e. estimate the error it will have on unseen data). The methodology may also be used to estimate the validation error and the generalisation error of the detection model 51, 52, 53, 54.

The term "validation error" refers to the error in the output of the detection model 51, 52, 53, 54 as applied to a set of patients used for validation, compared with the output when applied to patients that have not been used in training. Based on this error, a selection of model parameters (hyper-parameter tuning) may be made by choosing, amongst all the possible hyper-parameter combinations that have being trained (and their corresponding classification metrics stored in tables), one hyper-parameter combination that gives the high (optimal, or close to optimal) classification metric. As will be explained in more detail below, a possible classification metric may be the area under a receiver operating characteristic (ROC) curve.

The term "generalisation error" refers to the error that the detection model 51, 52, 53, 54 has on a set of patients that it has never seen (that is, patients that have not been included in its training). Mathematically speaking, it is not possible to know the actual error the model will have over a population it has never seen before. However, it is possible to provide a useful estimate of that error, by simulating an unseen population. This estimate may give an indication of the expected performance the detection model 51, 52, 53, 54 when it is used in the method of detecting cognitive impairment.

Figure 6A:
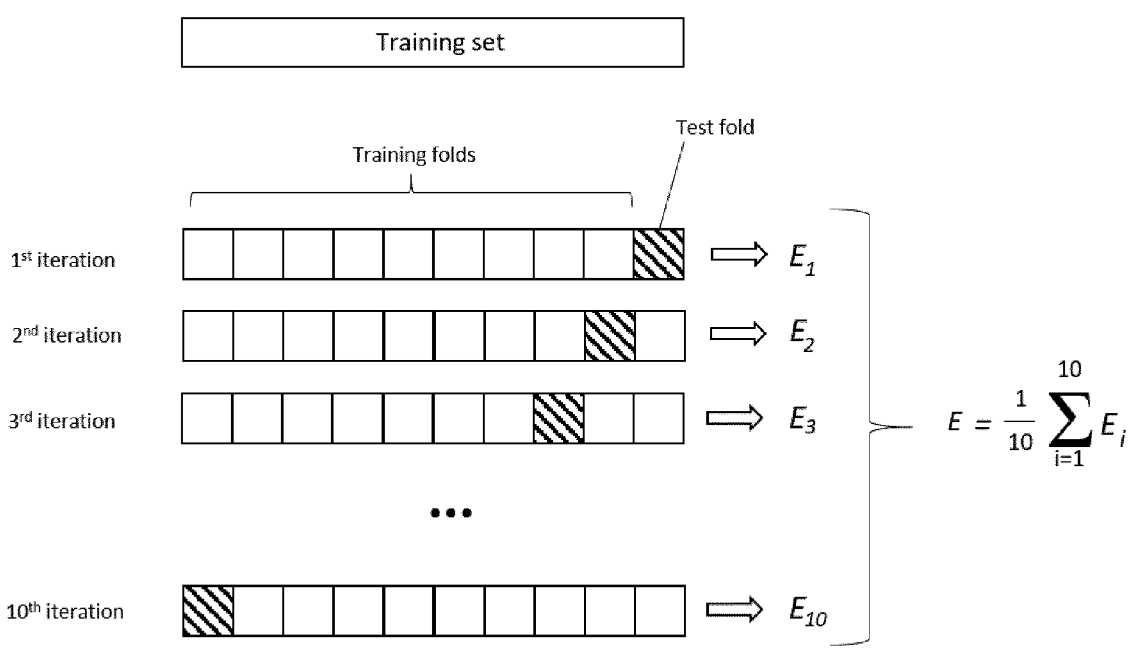
FIG. 6A depicts a cross-validation process for use in training a detection model.

In order to select the a combination of hyper-parameters that make up a detection model 51, 52, 53, 54, a strategy called cross validation (CV) may be used. With reference to FIG. 6A, this strategy may comprise in dividing the training set into K subsets (e.g. 10 subsets as shown), and, in each of the K iterations, a different subset may be used to validate and the rest to train. In this way, K validation errors may be obtained, and a global validation error may be defined as the average of the specific validation errors of each K. The optimal model may then be selected by choosing the set of model hyper-parameters that minimises or substantially reduces said error. Additionally, the K partitions may be made in a stratified way, i.e. by ensuring that the ratio of healthy and impaired patients in each validation subset is the same as in the training set.

Figure 7A:
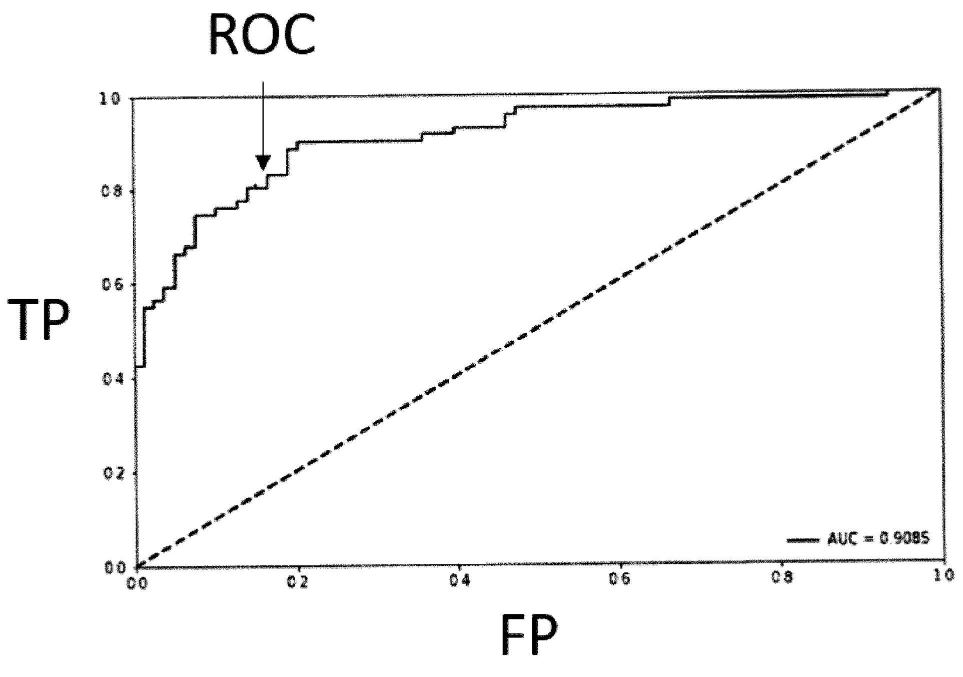
FIG. 7A depicts the receiver operating characteristic curve of an example implementation of the present disclosure.

An ROC curve may be plotted using the validation data, and example of which is shown in FIG. 7A. In FIG. 7A, the horizontal axis is the false positive rate (FP), and the vertical axis is true positive rate (TP). In general, a model which has no predictive capability (i.e. it produces random results) will have an ROC curve which is a straight diagonal line (i.e. the dotted line in FIG. 7A, shown as reference). The area under this reference ROC is 0.5. An ideal model (i.e. one which only ever produces true positives and no false positives) would have an ROC curve which has TP=1 for all values of FP, such that the area under the ROC curve is 1. As such, the area under the ROC curve gives a notion of the quality of the model (greater area being better quality), and may be used as a metric during validation, and may be used to select the model parameters.

Once the model parameters that make up the detection model 51, 52, 53, 54 have been chosen, a second validation may be carried out. The goal of the second validation is not to select model parameters, but to estimate the generalisation error of the detection model 51, 52, 53, 54. For this, with reference to FIG. 6B, a specific variant of cross-validation, known as leave-one-out cross-validation (LOOCV), may be used. As in FIG. 6A, there are K patients, corresponding to K iterations in the "outer loop" shown in FIG. 6B. According to this methodology, the chosen model may be trained again as explained above, but using the entire sample of patients except one. After that, a prediction may be generated for the remaining patient. This process may be repeated with all patients, resulting in a scoring (model result) for each of the patients.

Figure 6B:
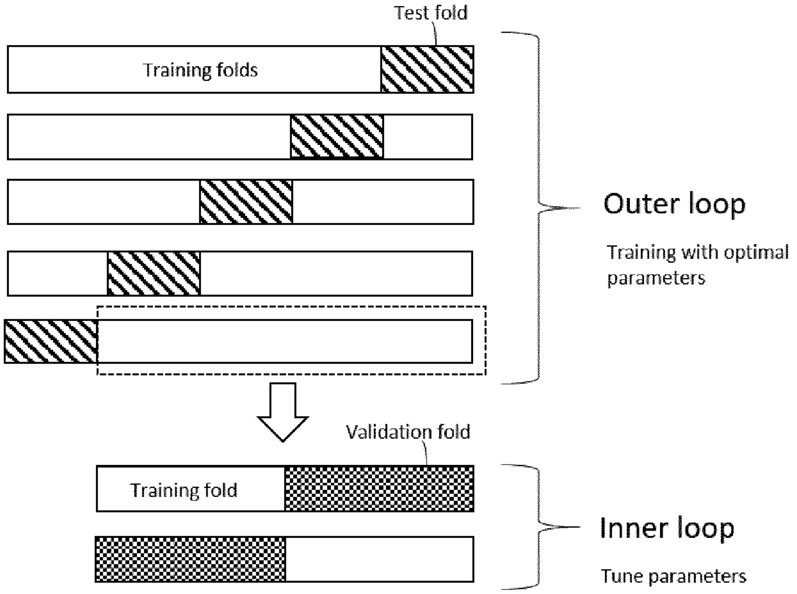
FIG. 6B depicts a nested cross-validation process for use in training a detection model and in estimating the generalisation error.

However, as shown in FIG. 6B, this is not a standard cross-validation. Each time the model is trained with K−1 patients in order to predict the outcome for the remaining patient, the methodology does not simply train over the previous model with already-selected hyper-parameters. Instead, a full train-validation process is performed over the K−1 patients, including a second cross-validation for selecting the best hyper-parameters for the same K−1 patients. In other words, according to this methodology, a nested cross validation may be performed, namely an outer leave-one-out cross-validation for estimating the generalisation error and, inside each one of the iterations of this outer CV, another internal cross-validation may be performed for tuning the model hyper-parameters.

Once the nested CV has been performed, a cut-off point (one of the model parameters) may be chosen for the detection model 51, 52, 53, 54 by using the K scoring values obtained in the process. This cut-off point may determine the positive-negative classification of the detection model 51, 52, 53, 54, i.e. an impairment probability 511, 521, 531, 541 above this cut-off point may indicate cognitive impairment (i.e. MCI/dementia), and an impairment probability 511, 521, 531, 541 below this cut-off point may indicate no impairment, or "healthy". The cut-off point may be set at different possible values, and for each of them the model will have different predictive characteristics.

Specifically, for a given value of the cut-off point, the following metrics may be calculated, which give a realistic estimate of the performance of the detection model 51, 52, 53, 54, with data that the model has never seen before:

Accuracy: Proportion of patients classified correctly versus all patients

Sensitivity (or "true positives"): Proportion of patients with cognitive impairment (MCI or dementia) classified correctly versus all patients with cognitive impairment (MCI or dementia)

Specificity (or "false positives"): Proportion of healthy patients classified correctly versus all healthy patients Area under the ROC: as shown in FIG. 7A, the ROC curve may provide a visualisation of the sensitivity of the classifier, on the Y axis, compared to the specificity of the classifier, on the X axis. The area under this curve may serve as a measure of the quality of the model, which, in addition, unlike accuracy, sensitivity or specificity, does not depend on the cut-off point chosen to balance the trade-off between sensitivity and specificity.

Therefore, given a collection of pluralities of test variables 410 and a collection of diagnoses 700 made by a clinician, the detection model 51 may be trained to take the collection of pluralities of test variables 410 as input and output a collection of values of impairment probability 511 such that a collection of indications (no impairment, MCI, dementia, etc.) obtained by applying one or more predetermined thresholds to the collection of values of impairment probability 511 closely or optimally matches the collection of diagnoses 700 made by the clinician.

FIG. 7A shows the ROC of an implementation of the present method of detecting cognitive impairment, using four neuropsychological tests described above, namely the memory test, the semantic verbal fluency test, the phonetic verbal fluency test, and the image description test. The detection models 51, 52, 53, 54 were trained with data from 154 patients. As can be seen, the area under the ROC in FIG. 7A is 0.9085, which is a good performance. As found by the present inventors, the present method is able to correctly distinguish patients with at least MCI (or more severe conditions) from patients with no cognitive impairment at all. Before the present invention was made, distinguishing patients with MCI from those with no cognitive impairment had been difficult due to poor performance. As such, the present method is particularly effective for use in large-scale screening of patients with MCI.

The final detection model 60 may be trained in a similar way to detection models 51, 52, 53, 54, as described above. With reference to FIG. 5, for the purpose of training the final detection model 60, on one hand, item 41 may be replaced by a calculation of the pluralities of test variables associated with any or all of the neuropsychological tests using detection models 51, 52, 53, 54 and/or the acoustic model 59 shown in FIG. 4 as desired, and each plurality of test variables 4111, 4112 may be replaced by a collection of impairment probabilities 501 corresponding to each patient P1, P2. On the other hand, the collection of diagnoses 700 made by the clinical practitioner C may be based on the collection of audio data 200, as before, but the audio data 201, 202 may each comprise recorded utterances made for each of the desired neuropsychological tests. Item 51 may be replaced by the final detection model 60.

Figure 7B:
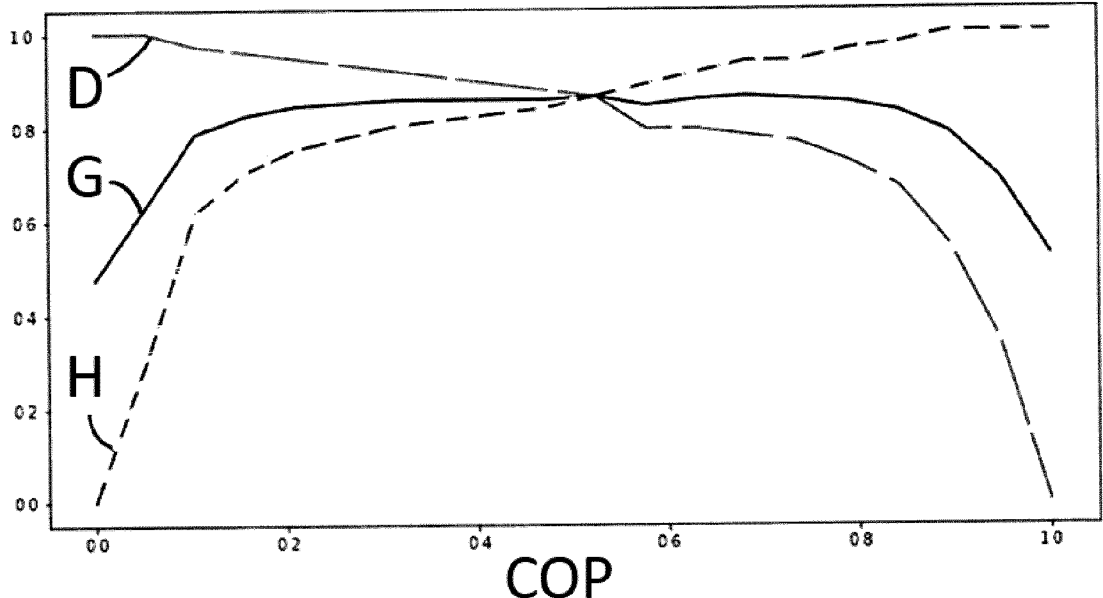
FIG. 7B depicts how sensitivity, specificity and global accuracy vary with cut-off probability.

Finally, as mentioned above, using the final impairment probability 601, an indication 70 may be made based on whether the final impairment probability 601 is above or below a predetermined threshold. The value of the predetermined threshold may affect the overall performance of the method of detecting cognitive impairment. FIG. 7B shows a number of accuracy curves demonstrating how sensitivity (curve D), specificity (curve H) and global accuracy (curve G) vary depending on the cut-off probability (COP), i.e. the predetermined threshold.

A chart such as shown in FIG. 7 may assist the operator in choosing the predetermined threshold so as to achieve the sensitivity-specificity balance that best suits the operator's needs. In certain applications, particular for screening purposes, a balance towards high sensitivity may be desirable, at the cost of a loss in specificity. In the implementation of the present method of detecting cognitive impairment as discussed above, it was possible to select a predetermined threshold to achieve high sensitivity whilst preserving a high level of global accuracy, which observed in the entire central part of FIG. 7 (approximate between 0.1 and 0.85).

It should be understood that the present invention can be used with any language, provided that the detection models are also trained using audio data in the respective language.

The present method of detecting cognitive impairment may be implemented as a computer program executing the steps of the different embodiments of the present method. Alternatively, the computer program may allow the disclosed elements of the present method to be enabled or disabled at will by the operator. In particular, the computer program may cause the computer to selectively execute the different embodiments of the present method. The selective execution may be based on a selection of the operator. The computer program may comprise instructions for receiving a selection of one or more of the available neuropsychological tests from the operator. As mentioned above, in general terms, the more different neuropsychological tests are used, the greater accuracy of the indication 70 of whether the patient suffers from cognitive impairment. However, this may come at a cost of a longer session due to the time necessary for the patient to complete all the tests. Therefore, especially for large-scale screening of MCI, a selection from the available neuropsychological tests may be used, so as to allow each patient to complete the session in a shorter time, thereby allowing more patients to be screened using the same resources. The operator may choose to use only some, or even just one, of the available neuropsychological tests as appropriate.

The methods of the present invention may be performed by computer systems comprising one or more computers. A computer used to implement the invention may comprise one or more processors, including general purpose CPUs, graphical processing units (GPUs), tensor processing units (TPU) or other specialised processors. A computer used to implement the invention may be physical or virtual. A computer used to implement the invention may be a server, a client or a workstation. Multiple computers used to implement the invention may be distributed and interconnected via a network such as a local area network (LAN) or wide area network (WAN). Individual steps of the method may be carried out by a computer system but not necessarily the same computer system. Results of a method of the invention may be displayed to a user or stored in any suitable storage medium. The present invention may be embodied in a non-transitory computer-readable storage medium that stores instructions to carry out a method of the invention. The present invention may be embodied in a computer system comprising one or more processors and memory or storage storing instructions to carry out a method of the invention.

Having described the invention it will be appreciated that variations may be made on the above described embodiments which are not intended to be limiting. The invention is defined in the appended claims and their equivalents.

REFERENCES

1. Influence of speaker de-identification in depression detection. Paula Lopez-Otero; Carmen Magariños; Laura Docio-Fernandez; Eduardo Rodriguez-Banga; Daniel Erro; Carmen Garcia-Mateo. IET Signal Processing. Year: 2017|Volume: 11, Issue: 9|Journal Article|Publisher: IET. htts://ieeexplore.ieee.org/stamp/stamp.jsp?tp=&arnumber=8221743
2. Lopez-Otero, P., Docio-Fernandez, L., Garcia-Mateo, C.: 'Assessing speaker independence on a speech-based depression level estimation system', Pattern Recognit. Lett., 2015, 68, pp. 343-350
3. Ortega-Garcia J, Fierrez J, Alonso-Fernandez F, Galbally J, Freire M R, Gonzalez-Rodriguez J et al. The Multiscenario multienvironment BioSecure Multimodal Database (BMDB). IEEE Trans Pattern Anal Mach Intell. 2010; 32(6):1097-1111. DOI 10.1109/TPAMI.2009.76
4. Michel Valstar, Björn Schuller, Kirsty Smith, Florian Eyben, Bihan Jiang, Sanjay Bilakhia, Sebastian Schnieder, Roddy Cowie, and Maja Pantic. 2013. AVEC 2013: the continuous audio/visual emotion and depression recognition challenge. In Proceedings of the 3rd ACM international workshop on Audio/visual emotion challenge (AVEC '13). ACM, New York, NY, USA, 3-10. DOI: https.//doi.org/10.1145/2512530.2512533

5. Morris, J. C., Heyman, A., Mohs, R. C., Hughes, J. P., van Belle, G., Fillenbaum, G., Mellits, E. D., & Clark, C. (1989). The consortium to establish a registry for Alzheimer's disease (CERAD): I. Clinical and neuropsychological assessment of Alzheimer's disease. Neurology, 39(9), 1159-1165
6. Troyer A K, Moscovitch M, Winocur G. Clustering and switching as two components of verbal fluency: evidence from younger and older healthy adults. Neuropsychology 1997; 11:138-46
7. Vaughan R M, Coen R F, Kenny R, Lawlor B A. Preservation of the semantic verbal fluency advantage in a large population-based sample: normative data from the TILDA Study. J Int Neuropsychol Soc. 2016; 22:570-576
8. Tröger, J., Linz, N., K"onig, A., Robert, P., Alexandersson, J., Peter, J., and Kray, J. (2019). Exploitation vs. exploration—computational temporal and semantic analysis explains semantic verbal fluency impairment in alzheimer's disease. Neuropsychologia, 131, 05.
9. Fraser, K. C., Meltzer, J. A., Rudzicz, F., 2016. Linguistic features identify Alzheimer's disease in narrative speech. J. Alzheimers Dis. 49, 407-422

The invention claimed is:

1. A computer-implemented method of detecting cognitive impairment comprising:

receiving audio data representing recorded utterances of a patient, the audio data having been generated by recording the utterances made by the patient when completing first and second neuropsychological tests, the second neuropsychological test being different from the first neuropsychological test, and the utterances having been made by the patient in response to, for each respective neuropsychological test, predetermined visual information being displayed or predetermined audible information being provided to prompt the patient to complete the neuropsychological test by making the utterances;

processing the audio data using a speech-to-text engine to produce a text transcription of the recorded utterances;

processing the text transcription to calculate a first plurality of test variables associated with the first neuropsychological test, and a second plurality of test variables associated with the second neuropsychological test;

after the processing the text transcription, calculating:

by applying a first trained detection model on the first plurality of test variables, a first impairment probability indicating a likelihood that the patient suffers from the cognitive impairment; and, by applying a second trained detection model on the second plurality of test variables, a second impairment probability indicating a likelihood that the patient suffers from the cognitive impairment; and indicating that the patient suffers from the cognitive impairment if a final impairment probability calculated based on the first and second impairment probabilities is above a predetermined threshold, and indicating that the patient does not suffer from the cognitive impairment if the final impairment probability is below the predetermined threshold.

2. The method of claim 1, wherein the first neuropsychological test comprises any one of:

a memory test;

a semantic verbal fluency test;

a phonetic verbal fluency test;

an image description test;

an open-subject spontaneous speech test;

a paragraph reading test; and a recalling a memory from childhood test.

3. The method of claim 2, wherein the memory test is for measuring one, two or all of: immediate episodic verbal memory, learning ability, and delayed episodic verbal memory of the patient.

4. The method of claim 3, wherein:

for measuring immediate episodic verbal memory, the plurality of test variables comprises one, two or all of: number of correct words, percentage of incorrect words, and average correct word closeness; or for measuring learning ability, the plurality of test variables comprises one, two, or all of: mean number of correct words, mean percentage of incorrect words, and mean average correct word closeness; or for measuring delayed episodic verbal memory, the plurality of test variables comprises one, two or all of: answer accuracy percentage, answer recall percentage, and answer precision percentage.

5. The method of claim 2, wherein the semantic verbal fluency test is for measuring one, two, three or all of: counting fluency, clustering and switching fluency, prototypicality, and temporal clustering.

6. The method of claim 5, wherein:

for measuring counting fluency, the plurality of test variables comprise one or both of: number of animals, and percentage of time of silence; or for measuring clustering and switching fluency, the plurality of test variables comprise one or both of: average animal cluster size, and average animal sub-cluster size; or for measuring prototypicality, the plurality of test variables comprise one or both of: average prototypicality, and average prototypicality of first ten animals; or for measuring temporal clustering, the plurality of test variables comprise one or both of: number of temporal clusters, and average temporal cluster size.

7. The method of claim 1, wherein the second neuropsychological test comprises a memory test or a semantic verbal fluency test.

8. The method of claim 7, wherein the first and second neuropsychological tests comprise, respectively, a memory test and a semantic verbal fluency test.

9. The method of claim 1, further comprising:

processing the text transcription to calculate third and fourth pluralities of test variables associated respectively with third and fourth neuropsychological tests, wherein the first, second, third and fourth neuropsychological tests are all different from one another; and calculating, by applying third and fourth trained detection models respectively to the third and fourth pluralities of test variables, third and fourth impairment probabilities, respectively, each indicating a likelihood that the patient suffers from the cognitive impairment;

wherein the final impairment probability is calculated based on the first, second, third and fourth impairment probabilities.

10. The method of claim 1, wherein the final impairment probability is calculated using a trained final detection model.

11. The method of claim 1, wherein indicating that the patient suffers from the cognitive impairment comprises:

indicating that the patient suffers from dementia if the final impairment probability is above a second predetermined threshold greater than the first predetermined threshold; and indicating that the patient suffers from mild cognitive impairment if the final impairment probability is between the first and second predetermined thresholds.

12. The method of claim 1, further comprising:

processing the audio data using a trained acoustic model, wherein the acoustic model outputs an acoustic-based impairment probability indicating a likelihood that the patient suffers from the cognitive impairment;

wherein the final impairment probability is calculated additionally based on the acoustic-based impairment probability.

13. The method of claim 12, wherein the acoustic model comprises a support vector machine.

14. The method of claim 12, wherein the acoustic model comprises extracting, from the audio data, a plurality of functionals according to AVEC 2013, wherein the functionals are selected using correlation-based feature selection.

15. The method of claim 1, further comprising:

receiving personal information of the patient including at least one of age, gender, education level, place of birth, native language, and country of residence;

wherein the final impairment is calculated additionally based on the personal information.

16. The method of claim 1, further comprising:

for each respective neuropsychological test, displaying predetermined visual information or providing predetermined audible information prompting the patient to complete the test by making utterances; and generating the audio data by recording the utterances.

17. A system comprising a mobile device and a data processing apparatus, wherein:

the mobile device configured to:

present, to the patient, for each respective neuropsychological test, predetermined visual information or predetermined audible information prompting the patient to complete the test by making utterances;

generate the audio data by recording the utterances; and transmit the audio data to the data processing apparatus; and the data processing apparatus is configured to perform the method of claim 1.

18. The system of claim 17, wherein the data processing apparatus is a remote server.

19. The system of claim 17, wherein the data processing apparatus is another mobile device.

20. A method of training first and second detection models for use in calculating test variables associated with first and second neuropsychological tests for detecting cognitive impairment of a patient, the method comprising:

for each of a plurality of patients:

conducting the first and second neuropsychological tests on the patient, wherein each of the first and second neuropsychological tests comprises displaying predetermined visual information or providing predetermined audible information prompting the patient to complete the test by making utterances;

receiving audio data representing recorded utterances made by the patient during the tests;

obtaining a first diagnosis made by a clinical practitioner listening to the recorded utterances made by the patient during the first neuropsychological test;

obtaining a second diagnosis made by the clinical practitioner listening to the recorded utterances made by the patient during the second neuropsychological test;

processing the audio data using a speech-to-text engine to produce a text transcription of the recorded utterances;

processing the text transcription to calculate a first plurality of test variables associated with the first neuropsychological test;

processing the text transcription to calculate a second plurality of test variables associated with the second neuropsychological test;

associating the first plurality of test variables with the clinical practitioner's first diagnosis for the patient;

training the first detection model using the first pluralities of test variables and the plurality of associated first diagnoses;

training the second detection model using the second pluralities of test variables and the plurality of associated second diagnoses;

for each of the plurality of patients:

calculating, by applying the trained first detection model on the first plurality of test variables, a first impairment probability;

calculating, by applying the trained second detection model on the second plurality of test variables, a second impairment probability;

obtaining a final diagnosis made by the clinical practitioner listening to the recorded utterances made by the patient during the first and second neuropsychological tests; and associating the first impairment probability and second impairment probability with the clinical practitioner's final diagnosis; and training the final detection model using the first impairment probabilities, the second impairment probabilities and the plurality of associated final diagnoses.

* * * * *